US011534084B1

(12) United States Patent
Bogey

(10) Patent No.: US 11,534,084 B1
(45) Date of Patent: Dec. 27, 2022

(54) GAIT TRAINING DEVICE

(71) Applicant: Ross Bogey, Spokane, WA (US)

(72) Inventor: Ross Bogey, Spokane, WA (US)

( * ) Notice: Subject to any disclaimer, the term of this patent is extended or adjusted under 35 U.S.C. 154(b) by 0 days.

(21) Appl. No.: 17/673,674

(22) Filed: Feb. 16, 2022

Related U.S. Application Data

(63) Continuation of application No. PCT/US2021/047184, filed on Aug. 23, 2021.

(51) Int. Cl.
*A61B 5/11* (2006.01)
*A61B 5/103* (2006.01)

(52) U.S. Cl.
CPC ............ *A61B 5/112* (2013.01); *A61B 5/1036* (2013.01); *A61H 2201/1652* (2013.01)

(58) Field of Classification Search
CPC ..... A61B 5/112; A61B 5/1036; A61B 5/1038; A61B 2562/0219; A61B 5/6807; A61B 5/6829; A61B 2562/0247; A61B 2505/09; A61H 2201/1652; A61H 2201/5061
See application file for complete search history.

(56) References Cited

U.S. PATENT DOCUMENTS

| | | |
|---|---|---|
| 4,813,436 A | 3/1989 | Au |
| 6,360,597 B1 | 3/2002 | Hubbard, Jr. |
| 6,666,831 B1 | 12/2003 | Edgerton |
| 6,689,075 B2 | 2/2004 | West |
| 6,836,744 B1 | 12/2004 | Asphahani |
| 6,895,341 B2 | 5/2005 | Barrey |
| 7,526,954 B2 | 5/2009 | Haselhurst |
| 7,632,239 B2 | 12/2009 | Dar |
| 7,756,585 B2 | 7/2010 | Embrey |
| 8,002,672 B2 | 8/2011 | Brunner |
| 8,261,611 B2 | 9/2012 | Kim |
| 8,460,162 B2 | 6/2013 | Park |
| 8,613,691 B2 | 12/2013 | Bosecker |
| 8,790,279 B2 | 7/2014 | Brunner |
| 8,968,218 B2 | 3/2015 | Wukasch |
| 9,302,046 B1 | 4/2016 | Giuffrida |
| 9,462,966 B2 | 10/2016 | Clausen |

(Continued)

FOREIGN PATENT DOCUMENTS

WO 2019175899 9/2019

*Primary Examiner* — Patrick Fernandes
(74) *Attorney, Agent, or Firm* — David A. Belasco; Belasco Jacobs & Townsley, PC

(57) ABSTRACT

A gait training device includes at least one surface electrode attached adjacent an identified muscle group of a user. The surface electrode measures muscle activity as electromyogram levels (EMG). First and second footswitch units have at least one footswitch disposed at an identified location adjacent the user's feet. First and second telemetry units are provided that attach to the legs of the user and are connected to the surface electrodes and the footswitch units. A computer has a connected telemetry data receiving device, audio and video output capabilities, data storage, computational capabilities and input devices. A computer program uses data from both footswitches and the at least one surface electrode to develop feedback information for the user that includes real-time data relating to muscle activity (EMG) that is correctly-timed, but excessive in amplitude, muscle activity that is correctly-timed, but with insufficient force and muscle activity that is out-of-phase or equinas.

78 Claims, 14 Drawing Sheets

(56) References Cited

U.S. PATENT DOCUMENTS

| | | |
|---|---|---|
| 9,480,618 B2 | 11/2016 | Hsiao-Wecksier |
| 9,498,401 B2 | 11/2016 | Herr |
| 9,974,478 B1 | 5/2018 | Brokaw |
| 2007/0173903 A1 | 7/2007 | Goren et al. |
| 2007/0275830 A1 | 11/2007 | Lee |
| 2010/0152629 A1 | 6/2010 | Haas, Jr. |
| 2013/0123665 A1 | 5/2013 | Mariani |
| 2014/0195023 A1 | 7/2014 | Statham |
| 2014/0276130 A1 | 9/2014 | Mirelman |
| 2015/0257679 A1 | 9/2015 | Ross |
| 2015/0260514 A1 | 9/2015 | Ménélas |
| 2016/0007885 A1 | 1/2016 | Basta |
| 2016/0302696 A1 | 10/2016 | Wilson |
| 2016/0331557 A1 | 11/2016 | Tong |
| 2017/0303849 A1 | 10/2017 | De Sapio |
| 2020/9093400 | 3/2020 | Hamner |
| 2020/0147382 A1 | 5/2020 | Caban |
| 2020/0147384 A1 * | 5/2020 | Caban ................ A61N 1/36139 |

* cited by examiner

GAIT TRAINING DEVICE

RELATED APPLICATION

The instant application is a continuation of PCT/US2021/047184, filed Aug. 23, 2021, currently pending and incorporating the disclosure thereof in its entirety.

FIELD OF INVENTION

This invention relates to the field of therapeutic medical training devices and more specifically to devices for retraining device users to walk while recovering from neuro-musculo-skeletal injury or disease.

BACKGROUND OF THE INVENTION

Individuals who suffer a stroke or other impairments of the nervous (and to a lesser extent) muscular systems such as Multiple Sclerosis, Parkinson's Disease, traumatic brain injury (TBI), acquired brain injury (tumor), cerebral palsy (CP) and spinal cord injury (SCI) will often require significant therapy to regain or augment their walking ability. Most persons in such therapy after a stroke will have hemiparesis issues.

Restoration of walking facility after neurological injury is a function of both recovery of 'normal' function plus reacquisition of motor skills that are independent of the expected normal recovery. Reacquisition of motor skills is related to the integration of several aspects of therapy. These can include massed practice (a proxy for number of correct repetitions) and more importantly the use of appropriate feedback which is uniquely provided by the present invention. This feedback is presented in real-time, and presents crucial information to both the therapy participant and the therapist regarding the muscle activity (or lack thereof) that leads to their poor walking ability. The invention shows therapy participants and therapists the type of abnormal muscle activation that needs to be corrected (excessive, insufficient, out-of-phase) and also provides feedback during the therapy session that details the amount of improvement during that session. Several important gait variables are calculated for the therapist during each therapy session (number of steps, stance and swing phase symmetry) which may be collated across therapy sessions to note which variables are most important in gait recovery training. The invention may also be used to identify muscle activity to the therapist to aid in fine-tuning future therapy sessions.

The following is a description of other related inventions designed to assist in the reacquisition of walking skills to injured or impaired device users.

Patent Application No. 2016/0007885, published for Basta et al., discloses methods of gait evaluation and a system to exercise those methods. The system comprises a number of sensors, including EMG. Patient worn and treadmill mounted sensors and data such as a user's heart rate and treadmill incline is captured through wireless heart rate monitoring sensors and gyroscopic or accelerometer sensors. The gait training system is capable of "providing a real-time measurement of a plurality of gait parameters for a user on the treadmill".

U.S. Patent Application No. 2014/0276130, published for Mirelman et al., is directed a method and a system for prediction, detection and treatment of gait abnormalities. The disclosed system with pressure and EMG sensors, provides a real-time feedback to a person on a treadmill. The information is presented on a screen. The reference takes into consideration the target population and the potential visual and perceptual changes occurring with age such as diminished depth perception, impaired peripheral vision and a decrease in signal definition.

U.S. Patent Application No. 2007/0275830, published for Lee et al., illustrates a gait training system that comprises piezoelectric pressure sensors and EMG sensors with a capability for real-time processing and feeding the data back to the patient, while the patient is walking on a treadmill. The reference discloses a control unit that can also display the gait data to a walker to appreciate his/her gait abnormality, and thereby the walker can have training to correct the abnormal gait by him/herself. For this purpose, the control unit may also include a display unit installed in front of the walker to display the gait data in diagrams or graphs to the walker.

U.S. Pat. No. 6,666,831, issued to Edgerton et al., is directed to a method and a system for people in rehabilitation after an injury. The system comprises an exoskeleton with pressure and EMG sensors. A condensed stepping performance is presented in real time on a monitor for a patient on a treadmill.

U.S. Patent Application No. 2014/0195023, published for Stratham et al., illustrates a method and a system for feedback on running style. The disclosed system includes EMG and pressure sensors and is capable providing real-time feedback information to a person about his reactivity. As described in the reference, "[t]he human interface may thus comprise a display providing a visual feedback signal to the user as a function of the calculated reactivity. The display may simply display a number that is proportional to the calculated reactivity and/or display a graph, e.g. a bar graph that extends as a function of the reactivity. The display could also provide a feedback by varying the signal of a displayed image as a function of the calculated reactivity."

U.S. Pat. No. 9,498,401, issued to Herr et al., discloses a system simulating a wearable device. The system has a number of sensors, including pressure and EMG sensors, and is capable of providing real-time control and analysis of the collected data. The robotic system of the invention provides a model on which to base designs for an ambulatory prosthetic for a subject.

U.S. Pat. No. 8,790,279, issued to Brunner, is directed to a gait analysis system for training or rehabilitation. The system in this reference comprises an array of pressure sensors with a display "which is placed in the visual field of the user and shows the user a simulation of a natural walking route". Feedback information presented to the user on a treadmill (stepping in a simulated puddle), can be signal coded.

U.S. Patent Application No. 2010/0152629, published for Haas Jr. et al., is directed to a system for rehabilitation/exercising. The system uses pressure and EMG sensors. Pressure and force sensors under the foot or sub-surface, collect in real time, data pertaining to the weight bearing, geometry of the feet and temporal and special and spatial parameters.

U.S. Pat. No. 6,895,341, issued to Barrey et al., is directed to a method for analyzing irregularities in human locomotion. Measurements, obtained from a number of sensors including an EMG device, are processed to analyze patient's gait. The processed information is "advantageously represented by coloured contours or a colour gradient".

It is an objective of the present invention to provide a device and system for retraining victims of stroke and other impairments of the nervous (and to a lesser extent) muscular systems to walk normally. It is a further objective to provide a system that uses visual and/or auditory feedback technology to speed and enhance the patient's recovery and retraining. It is a still further objective of the invention to provide this feedback in a real time mode. It is yet a further objective to provide the feedback data to a physical therapist in order to allow further refinements to the patient's therapy. It is still a further objective to provide a system to monitor and provide feedback to patients that need to address the pressure being exerted at different locations in their feet while recovering from foot and leg injuries. Finally, it is an objective of the present invention to provide these feedback-driven systems in training tools that provide a controlled and reliable routine to patients with durable and economical equipment.

While some of the objectives of the present invention are disclosed in the prior art, none of the inventions found include all of the requirements identified.

SUMMARY OF THE INVENTION

The present invention addresses all of the deficiencies of prior art gait training device inventions and satisfies all of the objectives described above.

(1) A gait training device providing the desired features may be constructed from the following components. At least one surface electrode is provided. The surface electrode is attached adjacent at least one identified muscle group of a device user. The at least one surface electrode measures muscle activity as electromyogram levels (EMG). The at least one identified muscle group is selected from a group that includes ankle plantar flexors ("calf", or triceps surae), dorsiflexors (pre-tibial muscles), peroneal muscles, knee extensors ("quadriceps"), hamstrings (primary knee flexors), hip flexors, (primary) hip extensors, hip adductors and hip abductors.

First and second footswitch units are provided. The footswitch units are in the nature of a shoe insole and are sized and shaped to fit beneath each foot of the device user. Each of the footswitch units has at least one footswitch disposed at an identified location on the units. The at least one identified location is selected from locations adjacent regions of a device user's heel (HEEL), 5th metatarsal head (5MT), 1st metatarsal head (1MT), and great toe (TOE) regions to indicate when the regions of a device user's foot are putting pressure on a walking surface.

First and second telemetry units are provided. The telemetry units are attached to the legs of the device user and are electrically connected to the surface electrodes and the footswitch units. A computer is provided. The computer has a connected telemetry data receiving device, audio and video output capabilities, data storage, computational capabilities and input devices. A computer program is provided. The computer program is installed on the computer and uses data from both footswitch units and the at least one surface electrode received through the telemetry data receiving device to develop feedback information for the device user.

The feedback information includes real-time data relating to muscle activity (EMG) that is correctly-timed, but excessive in amplitude, muscle activity that is correctly-timed, but with insufficient force and muscle activity that is out-of-phase. An apparatus is provided for providing the feedback information to the device user.

(2) In a variant of the invention, the feedback information is also provided to a therapist for the device user.

(3) In still another variant, the apparatus for providing the feedback information to the device user includes a signal video monitor. The video monitor is located in sight of the device user and receives the feedback information in a video format.

(4) In yet another variant, the apparatus for providing the feedback information to the device user includes either of headphones or a speaker system. The headphones or a speaker system receive the feedback information in an audio format and provide the feedback information the device user.

(5) In a further variant, a treadmill is provided. The treadmill provides a controlled walking surface for the device user.

(6) In still a further variant, an overhead suspension system is provided. The suspension system allows for off-loading for a portion of body weight of the device user during therapy.

(7) In yet a further variant, the footswitch positioned adjacent the device user's heel is movable with respect to each other footswitch to accommodate device users with different size feet.

(8) In another variant of the invention, the feedback information for muscle activity that is correctly-timed, but with insufficient force provides a display for the user that transitions from the first signal (BLACK) to a second signal (GRAY) to indicates the insufficient force.

(9) In still another variant, the feedback information for muscle activity that is correctly-timed, but excessive in amplitude provides a display for the user that transitions from a first signal (BLACK) to a third signal (YELLOW) to indicates the excessive amplitude.

(10) In yet another variant, the feedback information for muscle activity that is out-of-phase provides a display for the user that transitions from the first signal (BLACK) to a fourth signal (RED) to indicate the out-of-phase condition.

(11) In a further variant, the feedback information for muscle activity that is correctly-timed, but insufficient in force provides an auditory signal for the user that transitions from silence to a first tone to indicate the insufficient force.

(12) In still a further variant, the feedback information for muscle activity that is correctly-timed, but with excessive force provides an auditory signal for the user that transitions from silence to a second tone to indicate the excessive force.

(13) In yet a further variant, the feedback information for muscle activity that is out-of-phase provides an auditory signal for the user that transitions from silence to a third tone to indicate the phase out-of-phase condition.

(14) In another variant of the invention, the computer program provides an input screen for use by the therapist to indicate a leg and which of the identified muscle groups will be used by the program to provide feedback information.

(15) In still another variant, feedback information is provided for each phase of the device user's gait. The phases are identified as: weight acceptance, early single support, late single support, pre-swing, early swing and late swing.

(16) In yet another variant, the weight acceptance phase is indicated by footswitch data wherein (ipsilateral—same side as surface electrode—HEEL AND contralateral—opposite side from surface electrode—TOE footswitches are on) OR (ipsilateral 5MT AND contralateral TOE footswitches are on) OR (ipsilateral 1MT and contralateral TOE footswitches are on).

(17) In a further variant, the early single support phase is indicated by footswitch data wherein (ipsilateral HEEL OR ipsilateral 5MT OR ipsilateral 1MT footswitches are on) AND NOT (contralateral HEEL OR contralateral 5MT OR contralateral 1MT OR contralateral TOE footswitches are on).

(18) In still a further variant, the late single support phase is indicated by footswitch data wherein (ipsilateral HEEL OR ipsilateral 5MT OR ipsilateral 1MT OR ipsilateral TOE footswitches are on) AND NOT (contralateral HEEL OR contralateral 5MT OR contralateral 1MT OR contralateral TOE footswitches are on).

(19) In yet a further variant, the pre-swing phase is indicated by footswitch data wherein (ipsilateral TOE OR ipsilateral 5MT OR ipsilateral 1MT footswitches are on) AND (contralateral HEEL OR contralateral 5MT OR contralateral 1MT footswitches are on) AND NOT (ipsilateral HEEL footswitch is on) AND NOT (contralateral TOE footswitch is on).

(20) In another variant of the invention, the early swing phase is indicated by footswitch data wherein (contralateral HEEL OR contralateral 5MT OR contralateral 1MT footswitches are on) AND NOT (ipsilateral HEEL OR ipsilateral 5MT OR ipsilateral 1MT OR ipsilateral TOE footswitches are on).

(21) In still another variant, the late swing phase is indicated by footswitch data wherein (contralateral 5MT OR contralateral 1MT OR contralateral TOE footswitches are on) AND NOT (ipsilateral HEEL OR ipsilateral 5MT OR ipsilateral 1MT OR ipsilateral TOE footswitches are on).

(22) In yet another variant, an equinas gait condition is indicated by footswitch data during the weight acceptance phase wherein (ipsilateral TOE OR ipsilateral 5MT OR ipsilateral 1MT footswitches are on) AND (contralateral 5MT OR contralateral 1MT OR contralateral TOE footswitches are on) AND NOT (ipsilateral HEEL footswitch is on), the footswitch data is used to provide negative feedback (ORANGE) to either of the device user and the therapist.

(23) In a further variant, a contralateral single support phase for reinforcement purposes is indicated by footswitch data wherein (contralateral HEEL OR contralateral 5MT OR contralateral 1MT OR contralateral TOE footswitches are on) AND NOT (ipsilateral HEEL OR ipsilateral 5MT OR ipsilateral 1MT OR ipsilateral TOE footswitches are on) and an ispilateral single support phase for reinforcement purposes is indicated by footswitch data wherein (ipsilateral HEEL OR ipsilateral 5MT OR ipsilateral 1MT OR ipsilateral TOE footswitches are on) AND NOT (contralateral HEEL OR contralateral 5MT OR contralateral 1MT OR contralateral TOE footswitches are on).

(24) In still a further variant, a threshold duration of the contralateral single support phase (combination of the early and late contralateral single support phase durations) is determined and compared to a duration of the ispilateral single support phase (combination of the early and late ispilateral single support phase durations) and when the ispilateral single support phase exceeds the threshold duration of the contralateral single support phase a positive feedback signal (GREEN) is generated and provided to at least one of the device user and the therapist.

(25) In yet a further variant, a maximum EMG threshold intensity for the plantar flexors muscle group in the weight acceptance gait phase is 59 microvolts (mV), causing a fourth feedback signal (RED) for a portion of the gait phase that the measured EMG level is greater than the maximum EMG threshold intensity indicating an out-of-phase condition.

(26) In another variant of the invention, a minimum EMG threshold intensity for the plantar flexors muscle group in the early single support gait phase is 74 mV, causing a second feedback signal (GRAY) for a portion of the gait phase that the measured EMG level is less than the minimum EMG threshold intensity, and wherein a maximum EMG threshold intensity for the plantar flexors muscle group in the early single support gait phase is 118 mV, causing a third feedback signal (YELLOW) for a portion of the gait phase that the measured EMG level is greater than the maximum EMG threshold intensity.

(27) In still another variant, a minimum EMG threshold intensity for the plantar flexors muscle group in the late single support gait phase is 153 mV, causing a second feedback signal (GRAY) for a portion of the gait phase that the measured EMG level is less than the minimum EMG threshold intensity, and wherein a maximum EMG threshold intensity for the plantar flexors muscle group in the late single support gait phase is 191 mV, causing a third feedback signal (YELLOW) for a portion of the gait phase that the measured EMG level is greater than the maximum EMG threshold intensity.

(28) In yet another variant, a minimum EMG threshold intensity for the plantar flexors muscle group in the pre-swing gait phase is 88 mV, causing a second feedback signal (GRAY) for a portion of the gait phase that the measured EMG level is less than the minimum EMG threshold intensity, and wherein a maximum EMG threshold intensity for the plantar flexors muscle group in the pre-swing gait phase is 132 mV, causing a third feedback signal (YELLOW) for a portion of the gait phase that the measured EMG level is greater than the maximum EMG threshold intensity.

(29) In a further variant, a maximum EMG threshold intensity for the plantar flexors muscle group in the early swing gait phase is 59 mV, causing a fourth feedback signal (RED) for a portion of the gait phase that the measured EMG level is greater than the maximum EMG threshold intensity indicating an out-of-phase condition.

(30) In still a further variant, a maximum EMG threshold intensity for the plantar flexors muscle group in the late swing gait phase is 59 mV, causing a fourth feedback signal (RED) for a portion of the gait phase that the measured EMG level is greater than the maximum EMG threshold intensity indicating an out-of-phase condition.

(31) In yet a further variant, a minimum EMG threshold intensity for the dorsiflexors muscle group in the weight acceptance gait phase is 120 microvolts (mV), causing a second feedback signal (GRAY) for a portion of the gait phase that the measured EMG level is less than the minimum EMG threshold intensity.

(32) In another variant of the invention, a maximum EMG threshold intensity for the dorsiflexors muscle group in the early single support gait phase is 280 mV, causing a third feedback signal (YELLOW) for a portion of the gait phase that the measured EMG level is greater than the maximum EMG threshold intensity.

(33) In still another variant, a maximum EMG threshold intensity for the dorsiflexors muscle group in the late single support gait phase is 280 mV, causing a third feedback signal (YELLOW) for a portion of the gait phase that the measured EMG level is greater than the maximum EMG threshold intensity.

(34) In yet another variant, a maximum EMG threshold intensity for the dorsiflexors muscle group in the pre-swing gait phase is 260 mV, causing a third feedback signal (YELLOW) for a portion of the gait phase that the measured EMG level is greater than the maximum EMG threshold intensity.

(35) In a further variant, a minimum EMG threshold intensity for the dorsiflexors muscle group in the early swing gait phase is 118 mV, causing a second feedback signal (GRAY) for a portion of the gait phase that the measured EMG level is less than the minimum EMG threshold intensity, and wherein a maximum EMG threshold intensity for the dorsiflexors muscle group in the early swing gait phase is 880 mV, causing a third feedback signal (YELLOW) for a portion of the gait phase that the measured EMG level is greater than the maximum EMG threshold intensity.

(36) In still a further variant, a minimum EMG threshold intensity for the dorsiflexors muscle group in the late swing gait phase is 120 mV, causing a second feedback signal (GRAY) for a portion of the gait phase that the measured EMG level is less than the minimum EMG threshold intensity, and wherein a maximum EMG threshold intensity for the dorsiflexors muscle group in the late swing gait phase is 882 mV, causing a third feedback signal (YELLOW) for a portion of the gait phase that the measured EMG level is greater than the maximum EMG threshold intensity.

(37) In yet a further variant, a maximum EMG threshold intensity for the peroneal muscle group in the weight acceptance gait phase is 44 millivolts (mV), causing a fourth feedback signal (RED) for a portion of the gait phase that the measured EMG level is greater than the maximum EMG threshold intensity indicating an out-of-phase condition.

(38) In anther variant of the invention, a minimum EMG threshold intensity for the peroneal muscle group in the early single support gait phase is 74 mV, causing a second feedback signal (GRAY) for a portion of the gait phase that the measured EMG level is less than the minimum EMG threshold intensity, and wherein a maximum EMG threshold intensity for the peroneal muscle group in the early single support gait phase is 103 mV, causing a third feedback signal (YELLOW) for a portion of the gait phase that the measured EMG level is greater than the maximum EMG threshold intensity.

(39) In still another variant, a minimum EMG threshold intensity for the peroneal muscle group in the late single support gait phase is 118 mV, causing a second feedback signal (GRAY) for a portion of the gait phase that the measured EMG level is less than the minimum EMG threshold intensity, and wherein a maximum EMG threshold intensity for the peroneal muscle group in the late single support gait phase is 176 mV, causing a third feedback signal (YELLOW) for a portion of the gait phase that the measured EMG level is greater than the maximum EMG threshold intensity.

(40) In yet another variant, a minimum EMG threshold intensity for the peroneal muscle group in the pre-swing gait phase is 65 mV, causing a second feedback signal (GRAY) for a portion of the gait phase that the measured EMG level is less than the minimum EMG threshold intensity, and wherein a maximum EMG threshold intensity for the peroneal muscle group in the pre-swing gait phase is 120 mV, causing a third feedback signal (YELLOW) for a portion of the gait phase that the measured EMG level is greater than the maximum EMG threshold intensity.

(41) In a further variant, a maximum EMG threshold intensity for the peroneal muscle group in the early swing gait phase is 60 mV, causing a fourth feedback signal (RED) for a portion of the gait phase that the measured EMG level is greater than the maximum EMG threshold intensity indicating an out-of-phase condition.

(42) In still a further variant, a maximum EMG threshold intensity for the peroneal muscle group in the late swing gait phase is 60 mV, causing a fourth feedback signal (RED) for a portion of the gait phase that the measured EMG level is greater than the maximum EMG threshold intensity indicating an out-of-phase condition.

(43) In yet a further variant, a minimum EMG threshold intensity for the knee extensors muscle group in the weight acceptance gait phase is 162 millivolts (mV), causing a second feedback signal (GRAY) for a portion of the gait phase that the measured EMG level is less than the minimum EMG threshold intensity, and wherein a maximum EMG threshold intensity for the knee extensors muscle group in the weight acceptance gait phase is 456 mV, causing a third feedback signal (YELLOW) for a portion of the gait phase that the measured EMG level is greater than the maximum EMG threshold intensity.

(44) In another variant of the invention, a minimum EMG threshold intensity for the knee extensors muscle group in the early single support gait phase is 147 mV, causing a second feedback signal (GRAY) for a portion of the gait phase that the measured EMG level is less than the minimum EMG threshold intensity, and wherein a maximum EMG threshold intensity for the knee extensors muscle group in the early single support gait phase is 441 mV, causing a third feedback signal (YELLOW) for a portion of the gait phase that the measured EMG level is greater than the maximum EMG threshold intensity.

(45) In still another variant of the invention, a maximum EMG threshold intensity for the knee extensors muscle group in the late single support gait phase is 353 mV, causing a fourth feedback signal (RED) for a portion of the gait phase that the measured EMG level is greater than the maximum EMG threshold intensity indicating an out-of-phase condition.

(46) In yet another variant, a maximum EMG threshold intensity for the knee extensors muscle group in the pre-swing gait phase is 309 mV, causing a fourth feedback signal (RED) for a portion of the gait phase that the measured EMG level is greater than the maximum EMG threshold intensity indicating an out-of-phase condition.

(47) In a further variant, a maximum EMG threshold intensity for the knee extensors muscle group in the early swing gait phase is 147 mV, causing a fourth feedback signal (RED) for a portion of the gait phase that the measured EMG level is greater than the maximum EMG threshold intensity indicating an out-of-phase condition.

(48) In still a further variant, a minimum EMG threshold intensity for the knee extensors muscle group in the late swing gait phase is 44 mV, causing a second feedback signal (GRAY) for a portion of the gait phase that the measured EMG level is less than the minimum EMG threshold intensity, and wherein a maximum EMG threshold intensity for the knee extensors muscle group in the late swing gait phase is 235 mV, causing a third feedback signal (YELLOW) for a portion of the gait phase that the measured EMG level is greater than the maximum EMG threshold intensity.

(49) In yet a further variant, a minimum EMG threshold intensity for the hamstrings muscle group in the weight acceptance gait phase is 118 millivolts (mV), causing a second feedback signal (GRAY) for a portion of the gait phase that the measured EMG level is less than the minimum EMG threshold intensity, and wherein a maximum EMG threshold intensity for the hamstrings muscle group in the weight acceptance gait phase is 235 mV, causing a third feedback signal (YELLOW) for a portion of the gait phase that the measured EMG level is greater than the maximum EMG threshold intensity.

(50) In another variant of the invention, a minimum EMG threshold intensity for the hamstrings muscle group in the early single support gait phase is 53 mV, causing a second feedback signal (GRAY) for a portion of the gait phase that the measured EMG level is less than the minimum EMG threshold intensity, and wherein a maximum EMG threshold intensity for the hamstrings muscle group in the early single support gait phase is 188 mV, causing a third feedback signal (YELLOW) for a portion of the gait phase that the measured EMG level is greater than the maximum EMG threshold intensity.

(51) In still another variant, a maximum EMG threshold intensity for the hamstrings muscle group in the late single support gait phase is 176 mV, causing a fourth feedback signal (RED) for a portion of the gait phase that the measured EMG level is greater than the maximum EMG threshold intensity indicating an out-of-phase condition.

(52) In yet another variant, a maximum EMG threshold intensity for the hamstrings muscle group in the pre-swing gait phase is 103 mV, causing a fourth feedback signal (RED) for a portion of the gait phase that the measured EMG level is greater than the maximum EMG threshold intensity indicating an out-of-phase condition.

(53) In a further variant, a minimum EMG threshold intensity for the hamstrings muscle group in the early swing gait phase is 22 mV, causing a second feedback signal (GRAY) for a portion of the gait phase that the measured EMG level is less than the minimum EMG threshold intensity, and wherein a maximum EMG threshold intensity for the hamstrings muscle group in the early swing gait phase is 105 mV, causing a third feedback signal (YELLOW) for a portion of the gait phase that the measured EMG level is greater than the maximum EMG threshold intensity.

(54) In still a further variant, a minimum EMG threshold intensity for the hamstrings muscle group in the late swing gait phase is 44 mV, causing a second feedback signal (GRAY) for a portion of the gait phase that the measured EMG level is less than the minimum EMG threshold intensity, and wherein a maximum EMG threshold intensity for the hamstrings muscle group in the late swing gait phase is 132 mV, causing a third feedback signal (YELLOW) for a portion of the gait phase that the measured EMG level is greater than the maximum EMG threshold intensity.

(55) In yet a further variant, a wherein a maximum EMG threshold intensity for the hip flexors muscle group in the weight acceptance gait phase is 260 mV, causing a fourth feedback signal (RED) for a portion of the gait phase that the measured EMG level is greater than the maximum EMG threshold intensity indicating an out-of-phase condition.

(56) In another variant of the invention, a maximum EMG threshold intensity for the hip flexors muscle group in the early single support gait phase is 255 mV, causing a fourth feedback signal (RED) for a portion of the gait phase that the measured EMG level is greater than the maximum EMG threshold intensity indicating an out-of-phase condition.

(57) In still another variant, a maximum EMG threshold intensity for the hip flexors muscle group in the late single support gait phase is 250 mV, causing a fourth feedback signal (RED) for a portion of the gait phase that the measured EMG level is greater than the maximum EMG threshold intensity indicating an out-of-phase condition.

(58) In yet another variant, a minimum EMG threshold intensity for the hip flexors muscle group in the pre-swing gait phase is 15 mV, causing a second feedback signal (GRAY) for a portion of the gait phase that the measured EMG level is less than the minimum EMG threshold intensity, and wherein a maximum EMG threshold intensity for the hip flexors muscle group in the pre-swing gait phase is 265 mV, causing a third feedback signal (YELLOW) for a portion of the gait phase that the measured EMG level is greater than the maximum EMG threshold intensity.

(59) In a further variant, a minimum EMG threshold intensity for the hip flexors muscle group in the early swing gait phase is 29 mV, causing a second feedback signal (GRAY) for a portion of the gait phase that the measured EMG level is less than the minimum EMG threshold intensity, and wherein a maximum EMG threshold intensity for the hip flexors muscle group in the early swing gait phase is 294 mV, causing a third feedback signal (YELLOW) for a portion of the gait phase that the measured EMG level is greater than the maximum EMG threshold intensity.

(60) In still a further variant, a maximum EMG threshold intensity for the hip flexors muscle group in the late swing gait phase is 235 mV, causing a third feedback signal (YELLOW) for a portion of the gait phase that the measured EMG level is greater than the maximum EMG threshold intensity.

(61) In yet a further variant, a minimum EMG threshold intensity for the hip extensors muscle group in the weight acceptance gait phase is 123 millivolt (mV), causing a second feedback signal (GRAY) for a portion of the gait phase that the measured EMG level is less than the minimum EMG threshold intensity, and wherein a maximum EMG threshold intensity for the hip extensors muscle group in the weight acceptance gait phase is 241 mV, causing a third feedback signal (YELLOW) for a portion of the gait phase that the measured EMG level is greater than the maximum EMG threshold intensity.

(62) In another variant of the invention, a minimum EMG threshold intensity for the hip extensors muscle group in the early single support gait phase is 65 mV, causing a second feedback signal (GRAY) for a portion of the gait phase that the measured EMG level is less than the minimum EMG threshold intensity, and wherein a maximum EMG threshold intensity for the hip extensors muscle group in the early single support gait phase is 194 mV, causing a third feedback signal (YELLOW) for a portion of the gait phase that the measured EMG level is greater than the maximum EMG threshold intensity.

(63) In still another variant, a minimum EMG threshold intensity for the hip extensors muscle group in the late single support gait phase is 10 mV, causing a second feedback signal (GRAY) for a portion of the gait phase that the measured EMG level is less than the minimum EMG threshold intensity, and wherein a maximum EMG threshold intensity for the hip extensors muscle group in the late single support gait phase is 170 mV, causing a third feedback signal (YELLOW) for a portion of the gait phase that the measured EMG level is greater than the maximum EMG threshold intensity.

(64) In yet another variant, a maximum EMG threshold intensity for the hip extensors muscle group in the pre-swing gait phase is 103 mV, causing a fourth feedback signal (RED) for a portion of the gait phase that the measured EMG level is greater than the maximum EMG threshold intensity indicating an out-of-phase condition.

(65) In a further variant, a maximum EMG threshold intensity for the hip extensors muscle group in the early swing gait phase is 105 mV, causing a fourth feedback signal (RED) for a portion of the gait phase that the measured EMG level is greater than the maximum EMG threshold intensity indicating an out-of-phase condition.

(66) In still a further variant, a maximum EMG threshold intensity for the hip extensors muscle group in the late swing gait phase is 147 mV, causing a fourth feedback signal (RED) for a portion of the gait phase that the measured EMG level is greater than the maximum EMG threshold intensity indicating an out-of-phase condition.

(67) In yet a further variant, a maximum EMG threshold intensity for the hip adductors muscle group in the weight acceptance gait phase is 103 millivolts (mV), causing a fourth feedback signal (RED) for a portion of the gait phase that the measured EMG level is greater than the maximum EMG threshold intensity indicating an out-of-phase condition.

(68) In another variant of the invention, a maximum EMG threshold intensity for the hip adductors muscle group in the early single support gait phase is 88 mV, causing a fourth feedback signal (RED) for a portion of the gait phase that the measured EMG level is greater than the maximum EMG threshold intensity indicating an out-of-phase condition.

(69) In still another variant, a maximum EMG threshold intensity for the hip adductors muscle group in the late single support gait phase is 88 mV, causing a third feedback signal (YELLOW) for a portion of the gait phase that the measured EMG level is greater than the maximum EMG threshold intensity.

(70) In yet another variant, a minimum EMG threshold intensity for the hip adductors muscle group in the pre-swing gait phase is 28 mV, causing a second feedback signal (GRAY) for a portion of the gait phase that the measured EMG level is less than the minimum EMG threshold intensity, and wherein a maximum EMG threshold intensity for the hip adductors muscle group in the pre-swing gait phase is 235 mV, causing a third feedback signal (YELLOW) for a portion of the gait phase that the measured EMG level is greater than the maximum EMG threshold intensity.

(71) In a further variant, a minimum EMG threshold intensity for the hip adductors muscle group in the early swing gait phase is 44 mV, causing a second feedback signal (GRAY) for a portion of the gait phase that the measured EMG level is less than the minimum EMG threshold intensity, and wherein a maximum EMG threshold intensity for the hip adductors muscle group in the early swing gait phase is 265 mV, causing a third feedback signal (YELLOW) for a portion of the gait phase that the measured EMG level is greater than the maximum EMG threshold intensity.

(72) In still a further variant, a maximum EMG threshold intensity for the hip adductors muscle group in the late swing gait phase is 221 mV, causing a third feedback signal (YELLOW) for a portion of the gait phase that the measured EMG level is greater than the maximum EMG threshold intensity.

(73) In yet a further variant, a minimum EMG threshold intensity for the hip abductors muscle group in the weight acceptance gait phase is 59 millivolts (mV), causing a second feedback signal (GRAY) for a portion of the gait phase that the measured EMG level is less than the minimum EMG threshold intensity, and wherein a maximum EMG threshold intensity for the hip abductors muscle group in the weight acceptance gait phase is 412 mV, causing a third feedback signal (YELLOW) for a portion of the gait phase that the measured EMG level is greater than the maximum EMG threshold intensity.

(74) In another variant of the invention, a minimum EMG threshold intensity for the hip abductors muscle group in the early single support gait phase is 132 mV, causing a second feedback signal (GRAY) for a portion of the gait phase that the measured EMG level is less than the minimum EMG threshold intensity, and wherein a maximum EMG threshold intensity for the hip abductors muscle group in the early single support gait phase is 309 mV, causing a third feedback signal (YELLOW) for a portion of the gait phase that the measured EMG level is greater than the maximum EMG threshold intensity.

(75) In still another variant, a maximum EMG threshold intensity for the hip abductors muscle group in the late single support gait phase is 162 mV, causing a fourth feedback signal (RED) for a portion of the gait phase that the measured EMG level is greater than the maximum EMG threshold intensity indicating an out-of-phase condition.

(76) In yet another variant, a maximum EMG threshold intensity for the hip abductors muscle group in the pre-swing gait phase is 147 mV, causing a fourth feedback signal (RED) for a portion of the gait phase that the measured EMG level is greater than the maximum EMG threshold intensity indicating an out-of-phase condition.

(77) In a further variant, a maximum EMG threshold intensity for the hip abductors muscle group in the early swing gait phase is 132 mV, causing a fourth feedback signal (RED) for a portion of the gait phase that the measured EMG level is greater than the maximum EMG threshold intensity indicating an out-of-phase condition.

(78) In a final variant of the invention, a maximum EMG threshold intensity for the hip abductors muscle group in the late swing gait phase is 132 mV, causing a third feedback signal (YELLOW) for a portion of the gait phase that the measured EMG level is greater than the maximum EMG threshold intensity.

An appreciation of the other aims and objectives of the present invention and an understanding of it may be achieved by referring to the accompanying drawings and the detailed description of a preferred embodiment.

DETAILED DESCRIPTION OF THE
PREFERRED EMBODIMENT

The present invention addresses all of the deficiencies of prior art gait training device inventions and satisfies all of the objectives described above.

Figure 4:
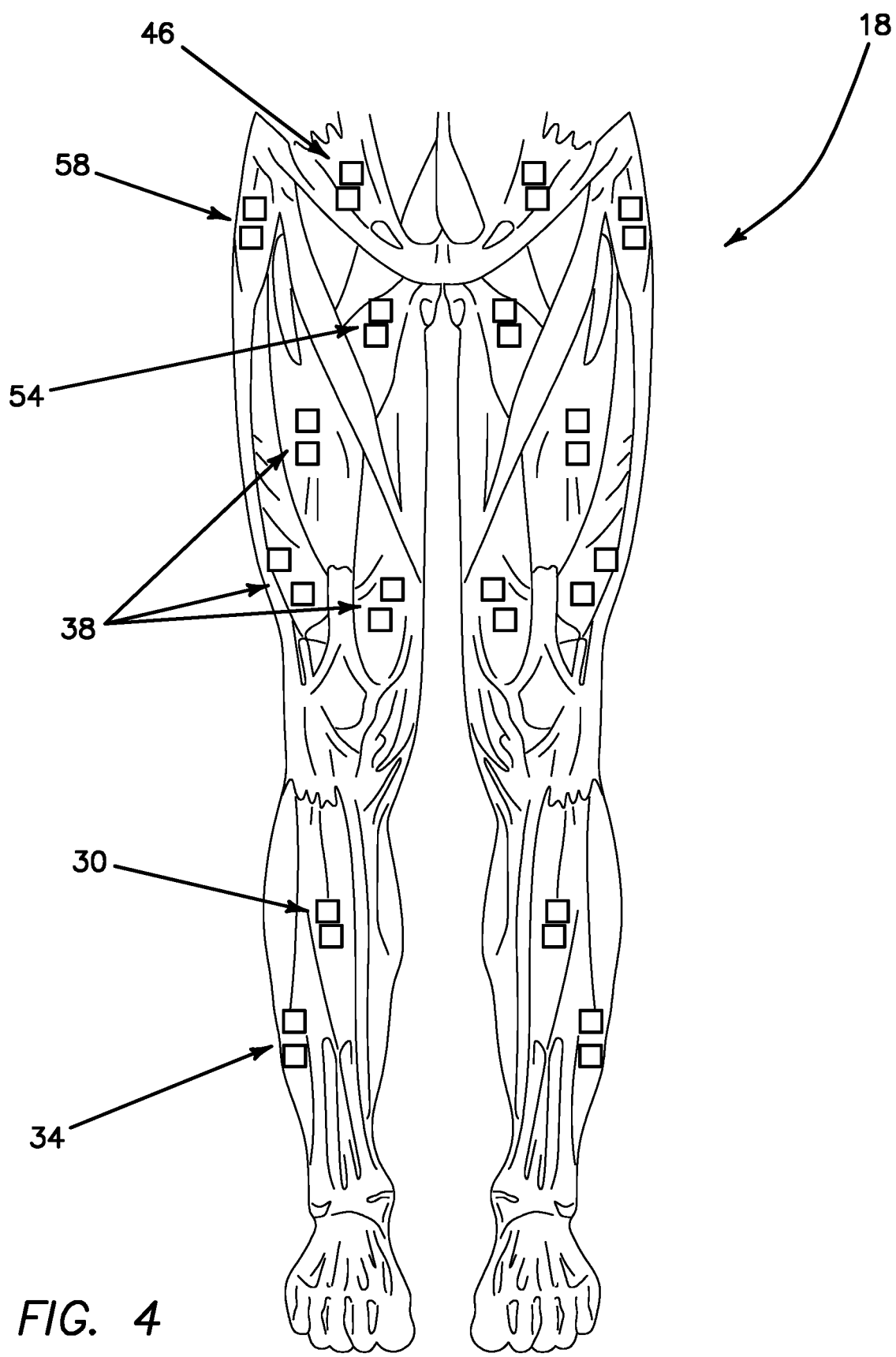
FIG. 4 is an anterior view of a device user's musculature illustrating placement points for surface electrodes on identified muscle groups.
Figure 5:
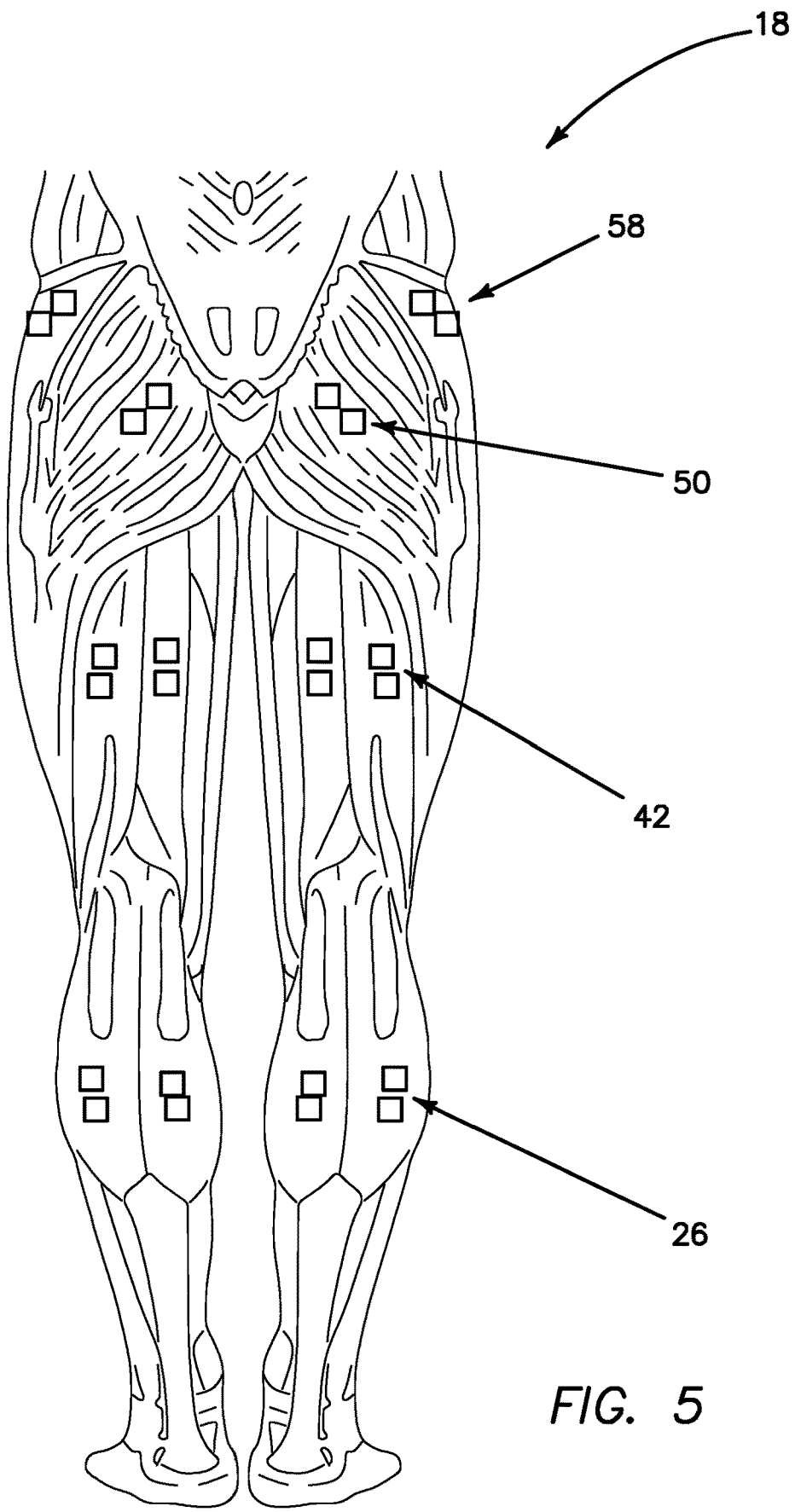
FIG. 5 is a posterior view of a device user's musculature illustrating placement points for surface electrodes on identified muscle groups.
Figure 6:
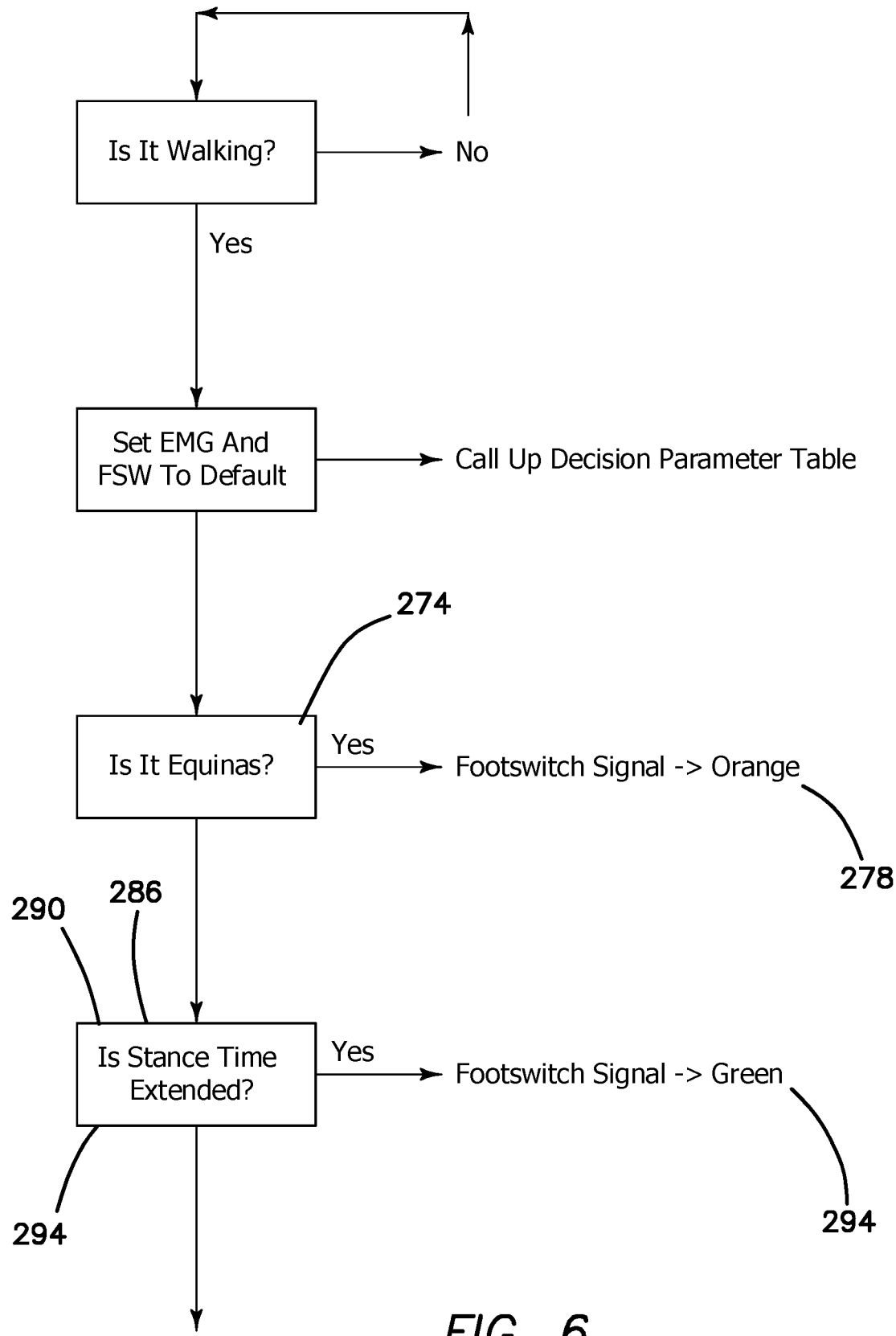
FIG. 6 is a flow chart illustrating initial setup of the Gait training Device and the methodology for providing feedback signals related to equinas gait and extended stance time.

(1) As illustrated in FIGS. 1-15, a gait training device 10 providing the desired features may be constructed from the following components. At least one surface electrode 14 is provided. The surface electrode 14 is attached adjacent at least one identified muscle group 18 of a device user 22. The at least one surface electrode 14 measures muscle activity as electromyogram levels (EMG). As illustrated in FIGS. 4 and 5, the at least one identified muscle group 18 is selected from a group that includes ankle plantar flexors 26 ("calf", or triceps surae), dorsiflexors 30 (pre-tibial muscles), peroneal muscles 34, knee extensors 38 ("quadriceps"), hamstrings 42 (primary knee flexors), hip flexors 46, (primary) hip extensors 50, hip adductors 54 and hip abductors 58.

Figure 10:
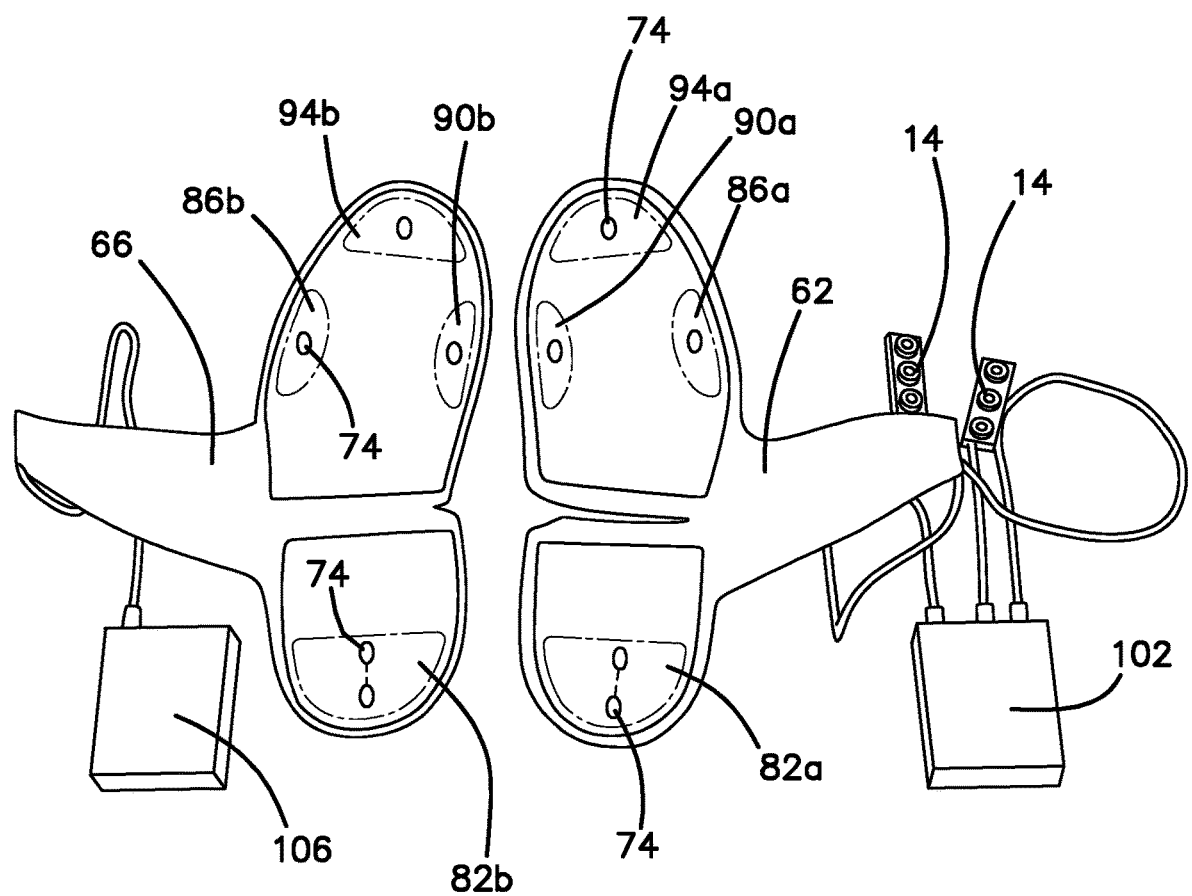
FIG. 10 is a top view of the first and second footswitch units, surface electrodes and first and second telemetry units.
Figure 15:
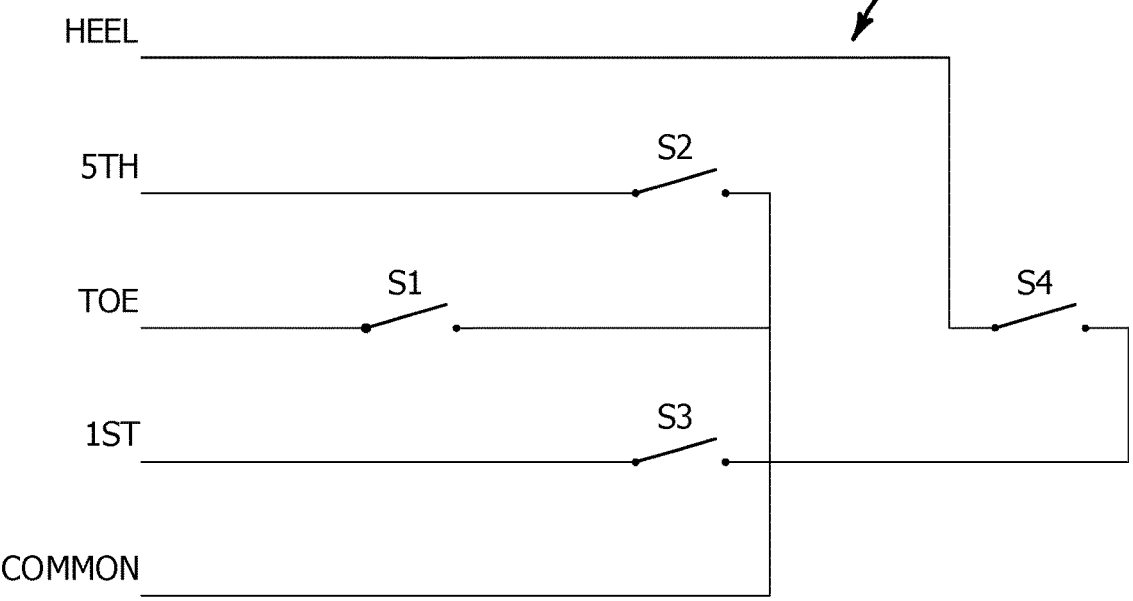
FIG. 15 is a schematic of the footswitch circuitry for invention.
Figure 11:
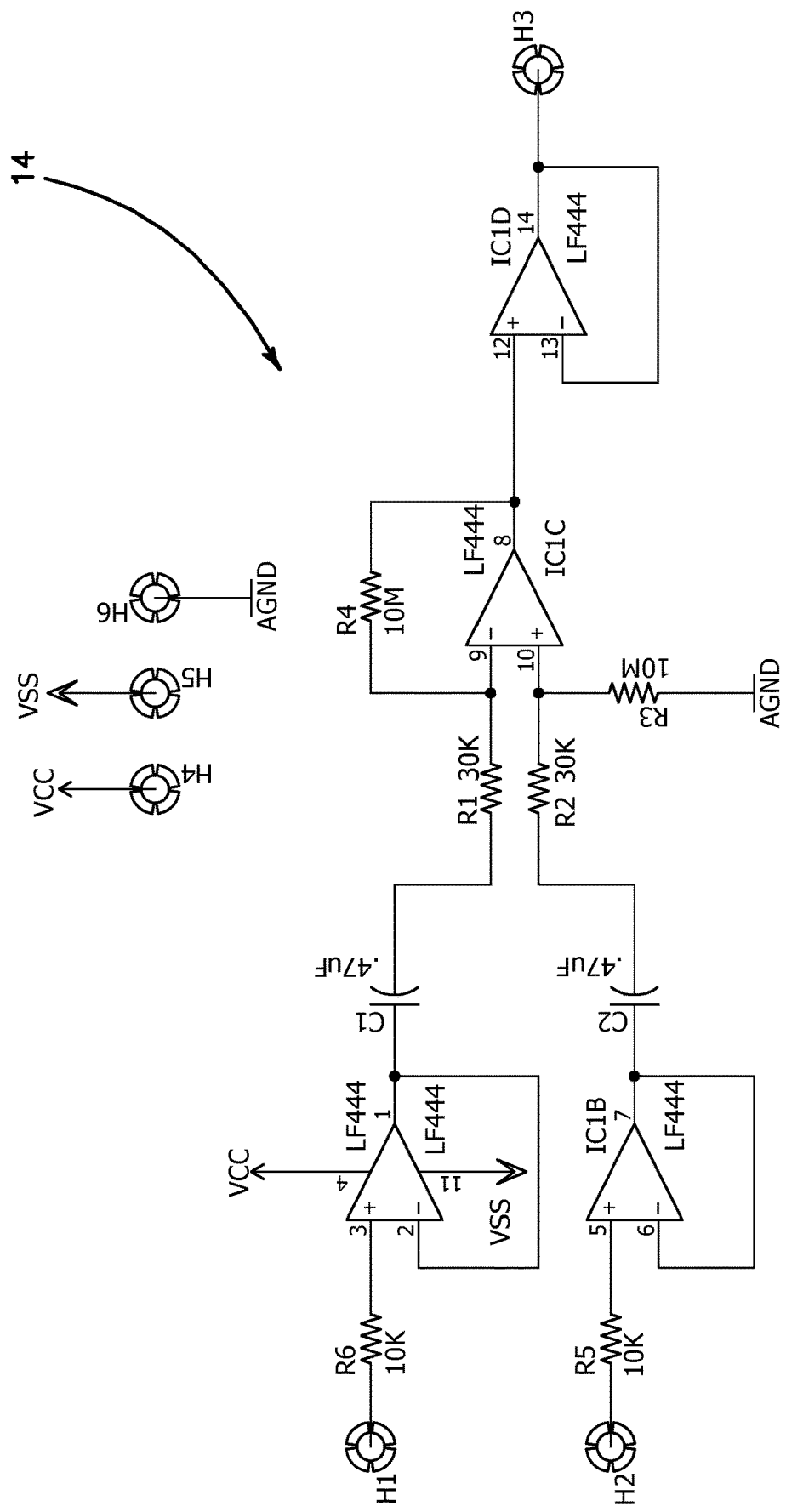
FIG. 11 is a schematic of the electrode circuitry for invention.
Figure 12:
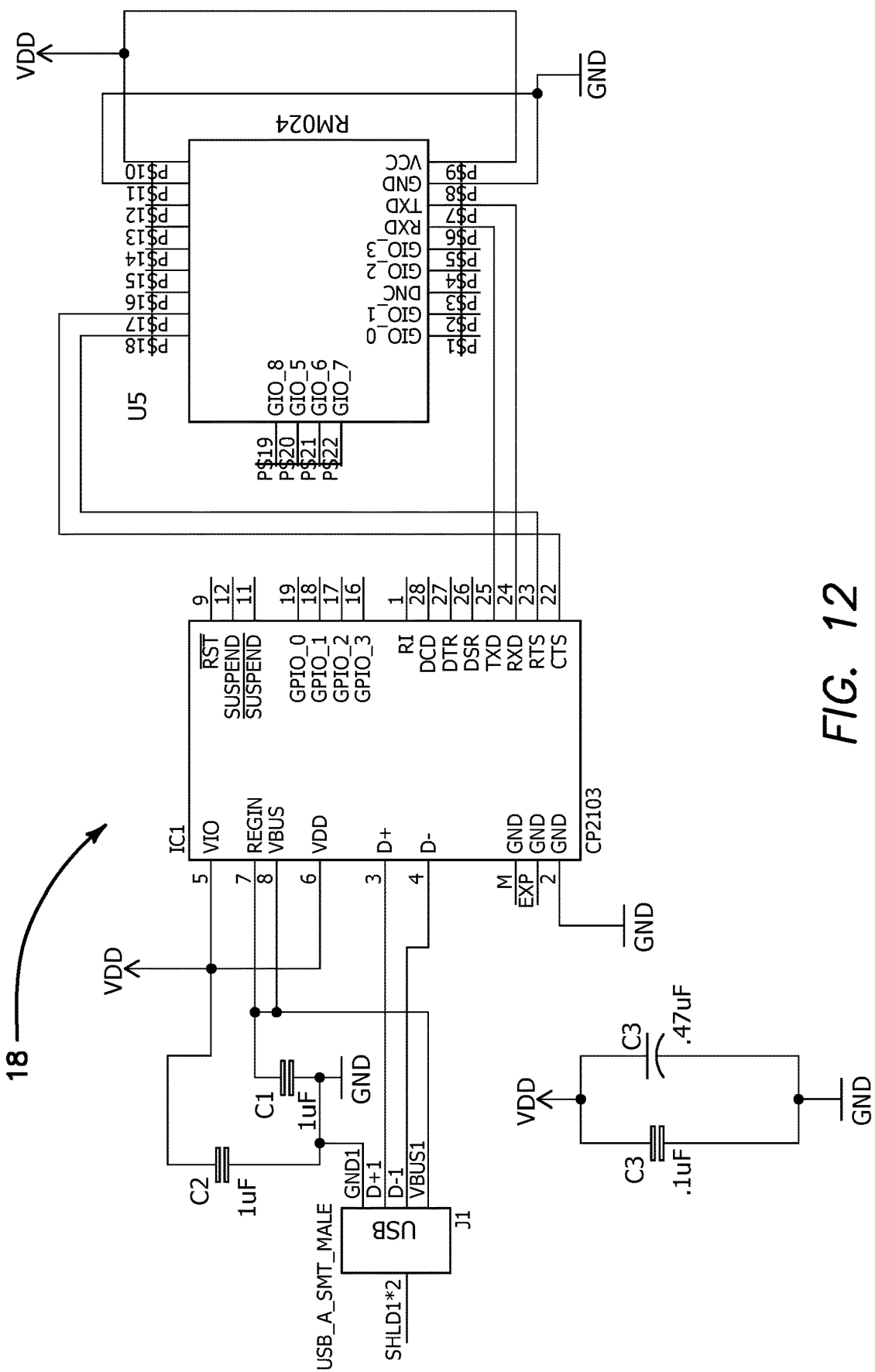
FIG. 12 is a schematic of the receiver circuitry for invention.
Figure 13:
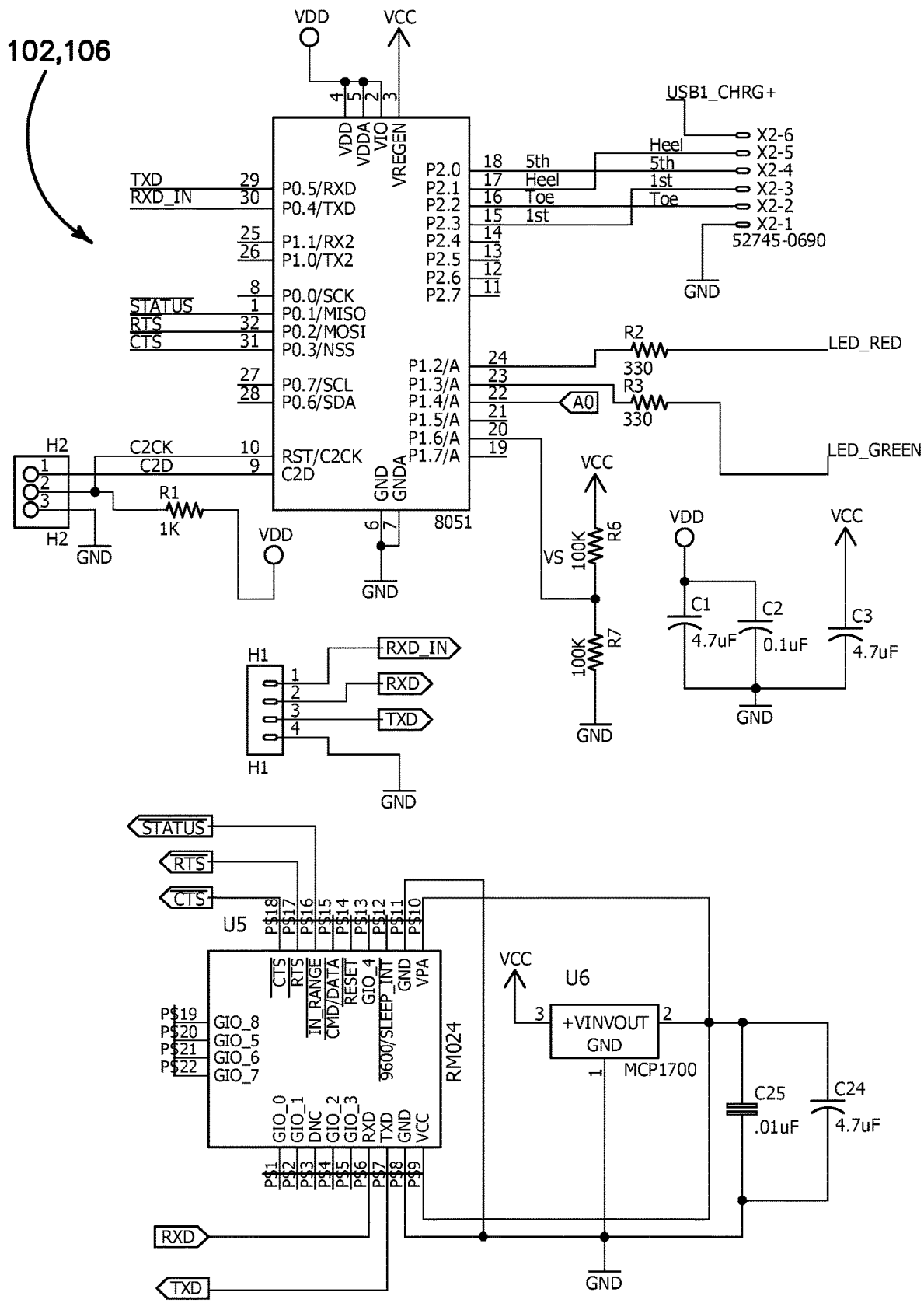
FIG. 13 is a first portion of a schematic of the transmitter circuitry for invention.
Figure 14:
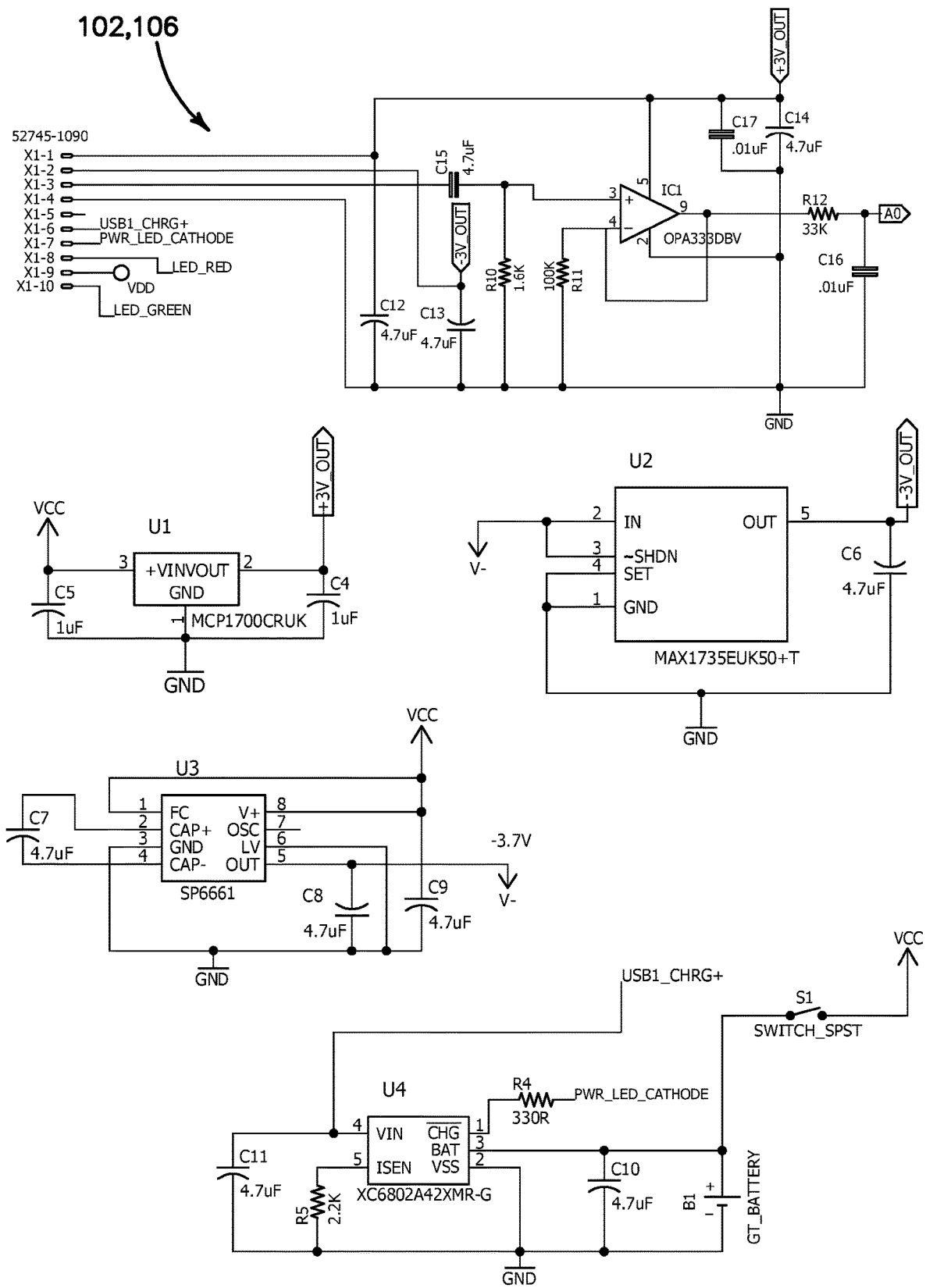
FIG. 14 is a second portion of a schematic of the transmitter circuitry for invention.

As illustrated in FIG. 10, first 62 and second 66 footswitch units are provided. The footswitch units 62, 66 are in the nature of a shoe insole and are sized and shaped to fit beneath each foot 70 of the device user 22. Each of the footswitch units 62, 66 has at least one footswitch 74 disposed at an identified location 78 on the units 62, 66. The at least one identified location 78 is selected from locations adjacent regions of a device user's heel (HEEL) 82, 5th metatarsal head (5MT) 86, 1st metatarsal head (1MT) 90, and great toe (TOE) 94 regions to indicate when the regions of a device user's foot 70 are putting pressure on a walking surface 98.

Figure 1:
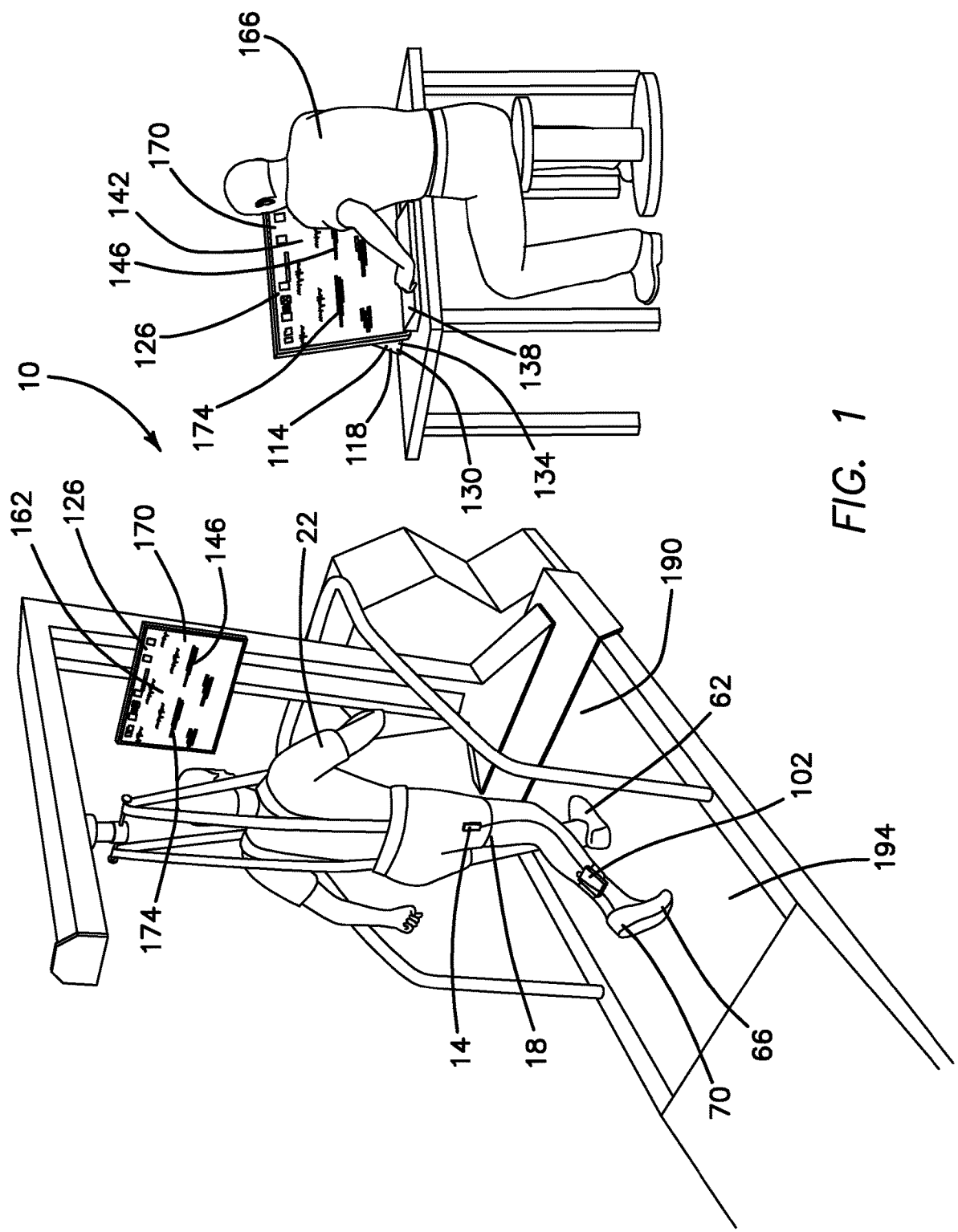
FIG. 1 is a perspective view of the preferred embodiment of the invention illustrating a device user suspended and walking on a treadmill with visual feedback provided to the device user and a therapist monitoring performance.
Figure 2:
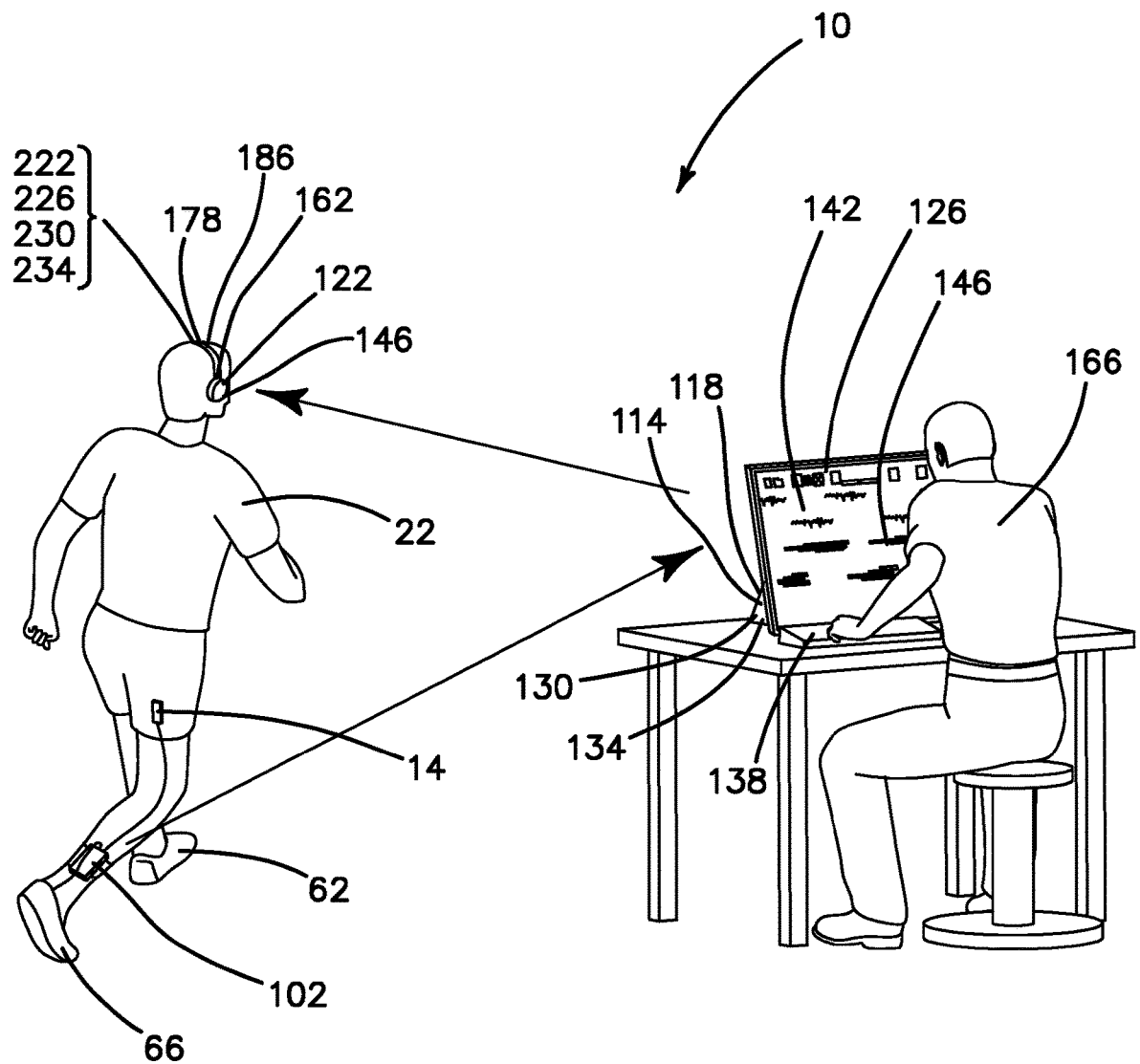
FIG. 2 is a perspective view of an alternative embodiment of the invention with the device user walking unaided over the ground and receiving auditory feedback through headphones while the therapist monitors performance on a screen.
Figure 3:
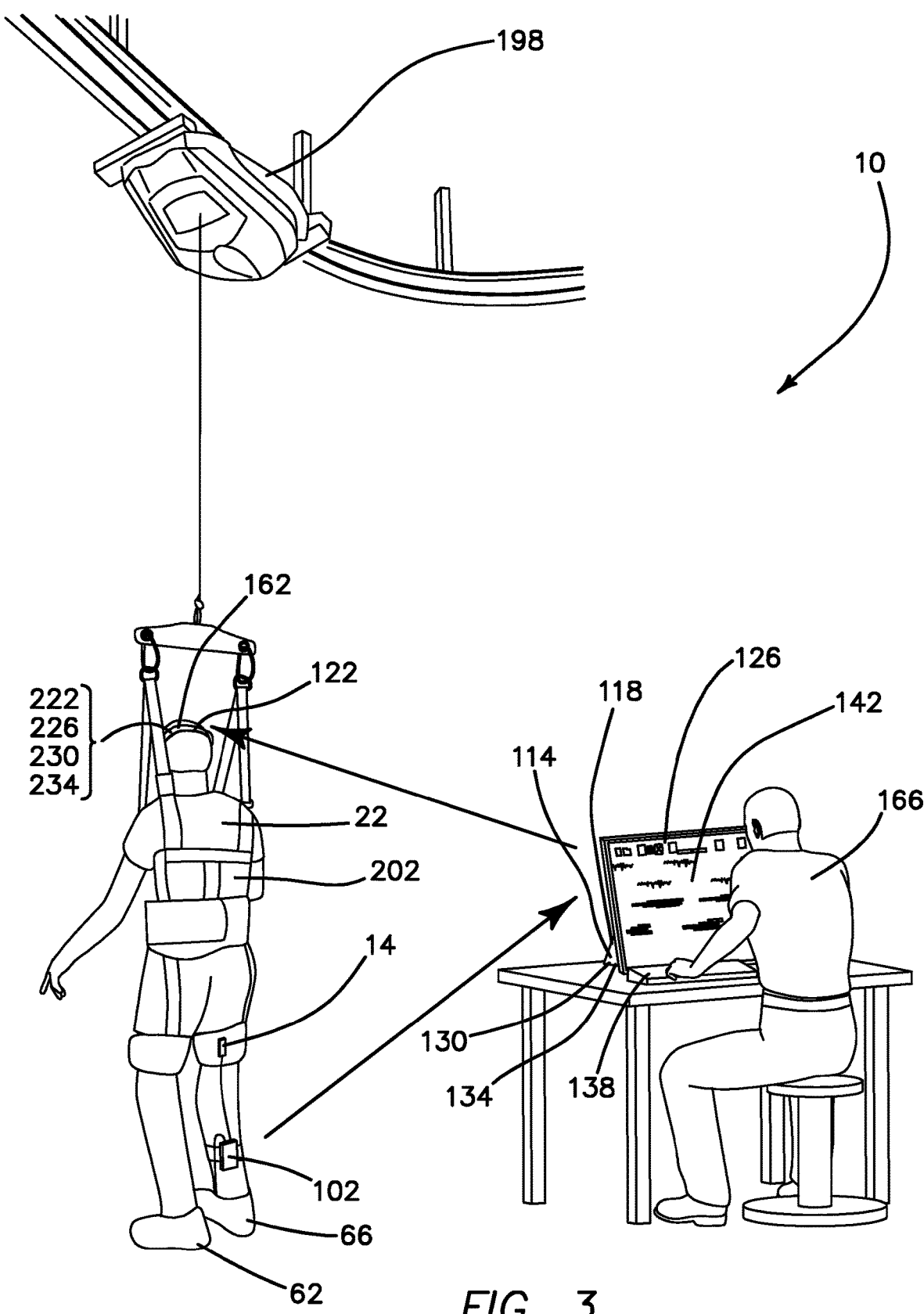
FIG. 3 is a perspective view of a second alternative embodiment of the invention with the device user walking with overhead support and receiving auditory feedback through headphones while the therapist monitors performance on a screen.

As illustrated in FIGS. 1-3, first 102 and second 106 telemetry units are provided. The telemetry units 102, 106 are attached to the legs 110 of the device user 22 and are electrically connected to the surface electrodes 14 and the footswitch units 62, 66. A computer 114 is provided. The computer 114 has a connected telemetry data receiving device 118, audio 122 and video 126 output capabilities, data storage 130, computational capabilities 134 and input devices 138. A computer program 142 is provided. The computer program 142 is installed on the computer 114 and uses data from both footswitch units 62, 66 and the at least one surface electrode 14 received through the telemetry data receiving device 118 to develop feedback information 146 for the device user 22.

As illustrated in FIGS. 6-9, the feedback information 146 includes real-time data relating to muscle activity (EMG) that is correctly-timed, but excessive in amplitude 150, muscle activity that is correctly-timed, but with insufficient force 154 and muscle activity that is out-of-phase 158. An apparatus 162 is provided for providing the feedback information 146 to the device user 22.

(2) In a variant of the invention, as illustrated in FIGS. 1-3, the feedback information 146 is also provided to a therapist 166 for the device user 22.

(3) In still another variant, the apparatus 162 for providing the feedback information 146 to the device user 22 includes a signal video monitor 170. The video monitor 170 is located in sight of the device user 22 and receives the feedback information 146 in a video format 174.

(4) In yet another variant, the apparatus 162 for providing the feedback information 146 to the device user 22 includes either of headphones 178 or a speaker system (not shown). The headphones 178 or a speaker system receive the feedback information 146 in an audio format 186 and provide the feedback information 146 the device user 22.

(5) In a further variant, as illustrated in FIG. 1, a treadmill 190 is provided. The treadmill 190 provides a controlled walking surface 194 for the device user 22.

(6) In still a further variant, as illustrated in FIG. 3, an overhead suspension system 198 is provided. The suspension system 198 allows for off-loading for a portion of body weight 202 of the device user 22 during therapy.

(7) In yet a further variant, as illustrated in FIG. 10, the footswitch 74 positioned adjacent the device user's heel 82 is movable with respect to each other footswitch 86, 90, 94 to accommodate device users 22 with different size feet 70.

Figure 7:
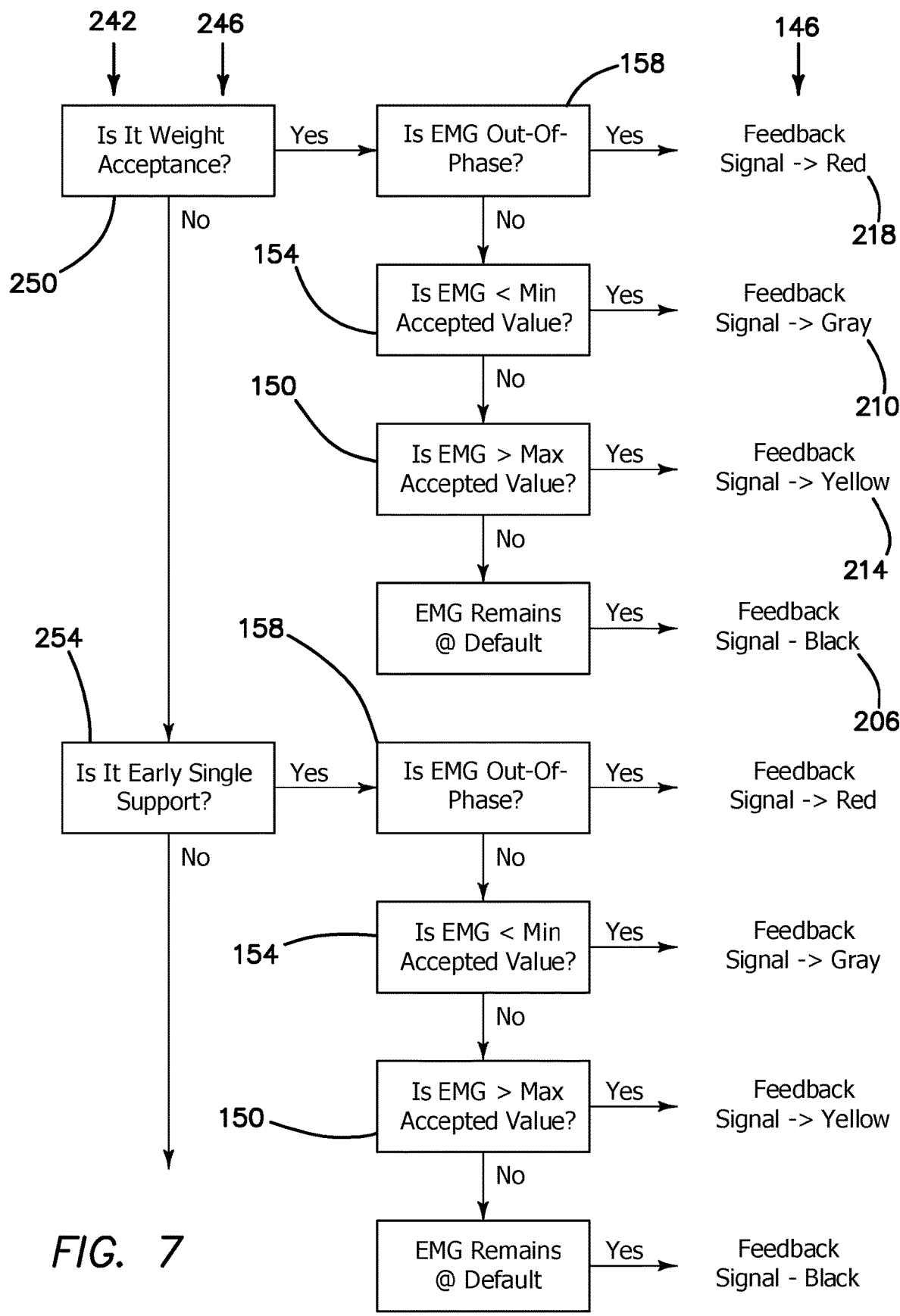
FIG. 7 is a flow chart illustrating the methodology for providing feedback signals for the Weight Acceptance and Early Single Support phases of the device user's gait.
Figure 8:
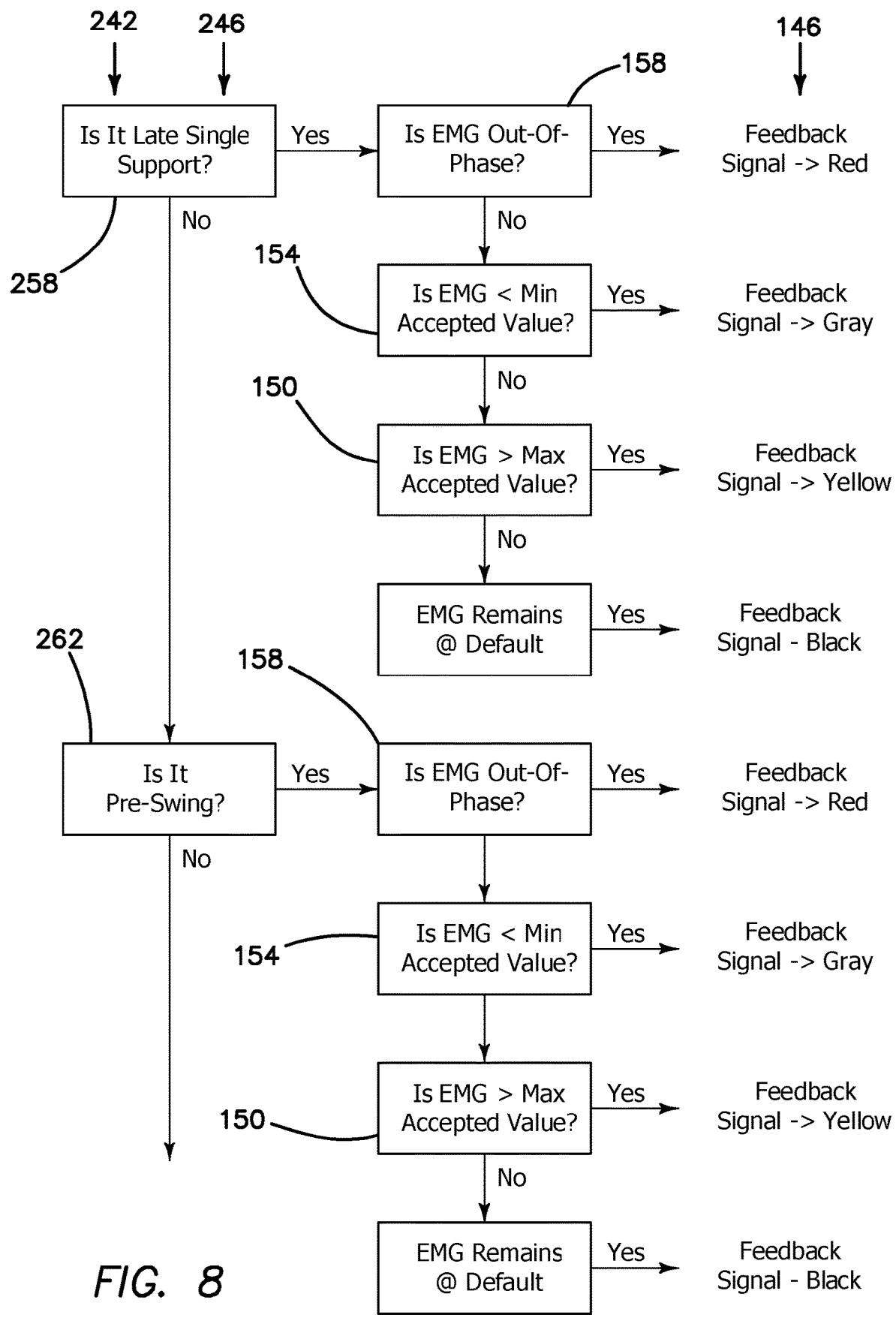
FIG. 8 is a flow chart illustrating the methodology for providing feedback signals for the Late Single Support and Pre-Swing phases of the device user's gait.
Figure 9:
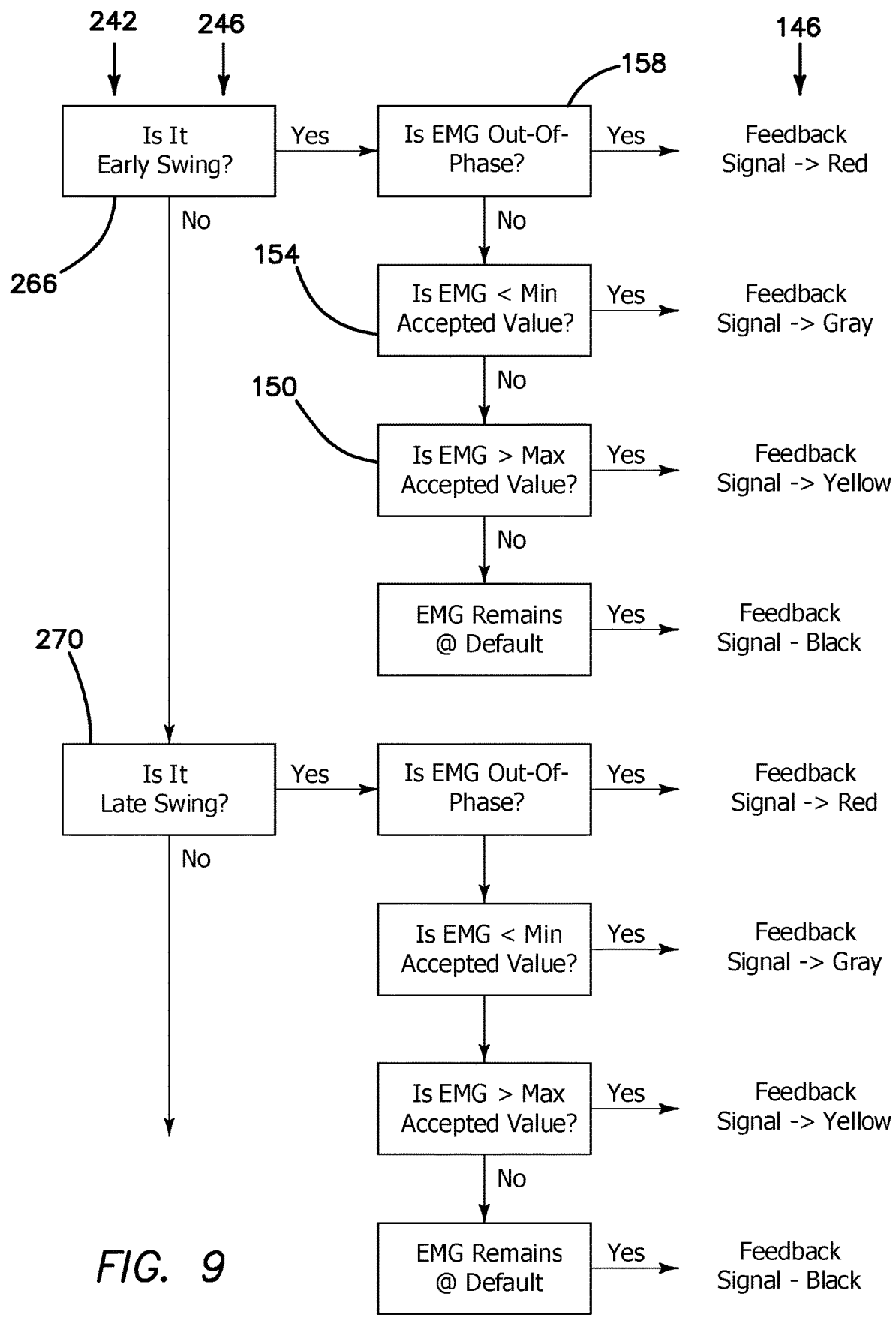
FIG. 9 is a flow chart illustrating the methodology for providing feedback signals for the Early Swing and Late Swing phases of the device user's gait.

(8) In another variant of the invention, as illustrated in FIGS. 7-9, the feedback information 146 for muscle activity that is correctly-timed, but with insufficient force 154 provides a display for the user 22 that transitions from the first signal (BLACK) 206 to a second signal (GRAY) 210 to indicates the insufficient force 154.

(9) In still another variant, the feedback information 146 for muscle activity that is correctly-timed, but excessive in amplitude 150 provides a display for the user 22 that transitions from a first signal (BLACK) 206 to a third signal (YELLOW) 214 to indicates the excessive amplitude 150.

(10) In yet another variant, the feedback information 146 for muscle activity that is out-of-phase 158 provides a display for the user 22 that transitions from the first signal (BLACK) 206 to a fourth signal (RED) 218 to indicate the out-of-phase condition 158.

(11) In a further variant, as illustrated in FIGS. 2 and 3, the feedback information for muscle activity that is correctly-timed, but insufficient in force 154 provides an auditory signal for the user 22 that transitions from silence 222 to a first tone 226 to indicate the insufficient force 154.

(12) In still a further variant, the feedback information for muscle activity that is correctly-timed, but with excessive force 150 provides an auditory signal for the user 22 that transitions from silence 222 to a second tone 230 to indicate the excessive force 150.

(13) In yet a further variant, the feedback information 146 for muscle activity that is out-of-phase 158 provides an auditory signal for the user 22 that transitions from silence 222 to a third tone 234 to indicate the phase out-of-phase condition 158.

(14) In another variant of the invention, the computer program 142 provides an input screen (not shown) for use by the therapist 166 to indicate a leg 110 and which of the identified muscle groups 18 will be used by the program 142 to provide feedback information 146.

(15) In still another variant, as illustrated in FIGS. 7-9, feedback information 146 is provided for each phase 242 of the device user's 22 gait 246. The phases 242 are identified as: weight acceptance 250, early single support 254, late single support 258, pre-swing 262, early swing 266 and late swing 270.

(16) In yet another variant, the weight acceptance phase 250 is indicated by footswitch data wherein (ipsilateral HEEL 82A AND contralateral TOE 94B footswitches are on) OR (ipsilateral 5MT 86A AND contralateral TOE 94B footswitches are on) OR (ipsilateral 1MT 90A and contralateral TOE 94B footswitches are on), NEW FIG. 10

(17) In a further variant, the early single support phase 254 is indicated by footswitch data wherein (ipsilateral HEEL 82A OR ipsilateral 5MT 86A OR ipsilateral 1MT 90A footswitches are on) AND NOT (contralateral HEEL 82B OR contralateral 5MT 86B OR contralateral 1MT 90B OR contralateral TOE 94B footswitches are on).

(18) In still a further variant, the late single support phase 258 is indicated by footswitch data wherein (ipsilateral HEEL 82A OR ipsilateral 5MT 86A OR ipsilateral 1MT 90A OR ipsilateral TOE 94A footswitches are on) AND NOT (contralateral HEEL 82B OR contralateral 5MT 86B OR contralateral 1MT 90B OR contralateral TOE 94B footswitches are on).

(19) In yet a further variant, the pre-swing phase 262 is indicated by footswitch data wherein (ipsilateral TOE 94A OR ipsilateral 5MT 86A OR ipsilateral 1MT 90A footswitches are on) AND (contralateral HEEL 82B OR contralateral 5MT 86B OR contralateral 1MT 90B footswitches are on) AND NOT (ipsilateral HEEL 82A footswitch is on) AND NOT (contralateral TOE 94B footswitch is on).

(20) In another variant of the invention, the early swing phase 266 is indicated by footswitch data wherein (contralateral HEEL 82B OR contralateral 5MT 86B OR contralateral 1MT 90B footswitches are on) AND NOT (ipsilateral HEEL 82A OR ipsilateral 5MT 86A OR ipsilateral 1MT 90A OR ipsilateral TOE 94A footswitches are on).

(21) In still another variant, the late swing phase 270 is indicated by footswitch data wherein (contralateral 5MT 86B OR contralateral 1MT 90B OR contralateral TOE 94B footswitches are on) AND NOT (ipsilateral HEEL 82A OR ipsilateral 5MT 86A OR ipsilateral 1MT 90A OR ipsilateral TOE 94A footswitches are on).

(22) In yet another variant, an equinas gait condition 274 is indicated by footswitch data during the weight acceptance phase 250 wherein (ipsilateral TOE 94A OR ipsilateral 5MT 86A OR ipsilateral 1MT 90A footswitches are on) AND (contralateral 5MT 86B OR contralateral 1MT 90B OR contralateral TOE 94B footswitches are on) AND NOT (ipsilateral HEEL 82A footswitch is on), the footswitch data is used to provide negative feedback (ORANGE) 278 to either of the device user 22 and the therapist 166.

(23) In a further variant, a contralateral single support phase for reinforcement purposes 282 is indicated by footswitch data wherein (contralateral HEEL 82B OR contralateral 5MT 86B OR contralateral 1MT 90B OR contralateral TOE 94B footswitches are on) AND NOT (ipsilateral HEEL 82A OR ipsilateral 5MT 86A OR ipsilateral 1MT 90A OR ipsilateral TOE 94A footswitches are on) and an ispilateral single support phase for reinforcement purposes 286 is indicated by footswitch data wherein (ipsilateral HEEL 82A OR ipsilateral 5MT 86A OR ipsilateral 1MT 90A OR ipsilateral TOE 94A footswitches are on) AND NOT (contralateral HEEL 82B OR contralateral 5MT 86B OR contralateral 1MT 90B OR contralateral TOE 94B footswitches are on).

(24) In still a further variant, a threshold duration of the contralateral single support phase 282 is determined and compared to a duration of the ispilateral single support phase 286 and when the ispilateral single support phase 286 exceeds the threshold duration 290 of the contralateral single support phase 282 a positive feedback signal (GREEN) 294 is generated and provided to at least one of the device user 22 and the therapist 166.

(25) In yet a further variant, a maximum EMG threshold intensity for the plantar flexors muscle group 26 in the weight acceptance gait phase 250 is 59 microvolts (mV), causing a fourth feedback signal (RED) 218 for a portion of the gait phase that the measured EMG level is greater than the maximum EMG threshold intensity indicating an out-of-phase condition 158.

(26) In another variant of the invention, a minimum EMG threshold intensity for the plantar flexors muscle group 26 in the early single support gait phase 254 is 74 mV, causing a second feedback signal (GRAY) 210 for a portion of the gait phase that the measured EMG level is less than the minimum EMG threshold intensity, and wherein a maximum EMG threshold intensity for the plantar flexors muscle group 26 in the early single support gait phase 254 is 118 mV, causing a third feedback signal (YELLOW) 214 for a portion of the gait phase that the measured EMG level is greater than the maximum EMG threshold intensity.

(27) In still another variant, a minimum EMG threshold intensity for the plantar flexors muscle group 26 in the late single support gait phase 258 is 153 mV, causing a second feedback signal (GRAY) 210 for a portion of the gait phase that the measured EMG level is less than the minimum EMG threshold intensity, and wherein a maximum EMG threshold intensity for the plantar flexors muscle group 26 in the late single support gait phase 258 is 191 mV, causing a third feedback signal (YELLOW) 214 for a portion of the gait phase that the measured EMG level is greater than the maximum EMG threshold intensity.

(28) In yet another variant, a minimum EMG threshold intensity for the plantar flexors muscle group 26 in the pre-swing gait phase 262 is 88 mV, causing a second feedback signal (GRAY) 210 for a portion of the gait phase that the measured EMG level is less than the minimum EMG threshold intensity, and wherein a maximum EMG threshold intensity for the plantar flexors muscle group 26 in the pre-swing gait phase is 132 mV, causing a third feedback signal (YELLOW) 214 for a portion of the gait phase that the measured EMG level is greater than the maximum EMG threshold intensity.

(29) In a further variant, a maximum EMG threshold intensity for the plantar flexors muscle group 26 in the early swing gait phase 266 is 59 mV, causing a fourth feedback signal (RED) 218 for a portion of the gait phase that the measured EMG level is greater than the maximum EMG threshold intensity indicating an out-of-phase condition 158.

(30) In still a further variant, a maximum EMG threshold intensity for the plantar flexors muscle group 26 in the late swing gait phase 270 is 59 mV, causing a fourth feedback signal (RED) 218 for a portion of the gait phase that the measured EMG level is greater than the maximum EMG threshold intensity indicating an out-of-phase condition 158.

(31) In yet a further variant, a minimum EMG threshold intensity for the dorsiflexors muscle group 30 in the weight acceptance gait phase 250 is 120 microvolts (mV), causing a second feedback signal (GRAY) 210 for a portion of the gait phase that the measured EMG level is less than the minimum EMG threshold intensity.

(32) In another variant of the invention, a maximum EMG threshold intensity for the dorsiflexors muscle group 30 in the early single support gait phase 254 is 280 mV, causing a third feedback signal (YELLOW) 214 for a portion of the gait phase that the measured EMG level is greater than the maximum EMG threshold intensity.

(33) In still another variant, a maximum EMG threshold intensity for the dorsiflexors muscle group 30 in the late single support gait phase 258 is 280 mV, causing a third feedback signal (YELLOW) 214 for a portion of the gait phase that the measured EMG level is greater than the maximum EMG threshold intensity.

(34) In yet another variant, a maximum EMG threshold intensity for the dorsiflexors muscle group 30 in the pre-swing gait phase 262 is 260 mV, causing a third feedback signal (YELLOW) 214 for a portion of the gait phase that the measured EMG level is greater than the maximum EMG threshold intensity.

(35) In a further variant, a minimum EMG threshold intensity for the dorsiflexors muscle group 30 in the early swing gait phase 266 is 118 mV, causing a second feedback signal (GRAY) 210 for a portion of the gait phase that the measured EMG level is less than the minimum EMG threshold intensity, and wherein a maximum EMG threshold intensity for the dorsiflexors muscle group 30 in the early swing gait phase 266 is 880 mV, causing a third feedback signal (YELLOW) 214 for a portion of the gait phase that the measured EMG level is greater than the maximum EMG threshold intensity.

(36) In still a further variant, a minimum EMG threshold intensity for the dorsiflexors muscle group 30 in the late swing gait phase 270 is 120 mV, causing a second feedback signal (GRAY) 210 for a portion of the gait phase that the measured EMG level is less than the minimum EMG threshold intensity, and wherein a maximum EMG threshold intensity for the dorsiflexors muscle group 30 in the late swing gait phase 270 is 882 mV, causing a third feedback signal (YELLOW) 214 for a portion of the gait phase that the measured EMG level is greater than the maximum EMG threshold intensity.

(37) In yet a further variant, a maximum EMG threshold intensity for the peroneal muscle group 34 in the weight acceptance gait phase 250 is 44 millivolts (mV), causing a fourth feedback signal (RED) 218 for a portion of the gait phase that the measured EMG level is greater than the maximum EMG threshold intensity indicating an out-of-phase condition 158.

(38) In anther variant of the invention, a minimum EMG threshold intensity for the peroneal muscle group 34 in the early single support gait phase 254 is 74 mV, causing a second feedback signal (GRAY) 210 for a portion of the gait phase that the measured EMG level is less than the minimum EMG threshold intensity, and wherein a maximum EMG threshold intensity for the peroneal muscle group 34 in the early single support gait phase 254 is 103 mV, causing a third feedback signal (YELLOW) 214 for a portion of the gait phase that the measured EMG level is greater than the maximum EMG threshold intensity.

(39) In still another variant, a minimum EMG threshold intensity for the peroneal muscle group 34 in the late single support gait phase 258 is 118 mV, causing a second feedback signal (GRAY) 210 for a portion of the gait phase that the measured EMG level is less than the minimum EMG threshold intensity, and wherein a maximum EMG threshold intensity for the peroneal muscle group 34 in the late single support gait phase 258 is 176 mV, causing a third feedback signal (YELLOW) 214 for a portion of the gait phase that the measured EMG level is greater than the maximum EMG threshold intensity.

(40) In yet another variant, a minimum EMG threshold intensity for the peroneal muscle group 34 in the pre-swing gait phase 262 is 65 mV, causing a second feedback signal (GRAY) 210 for a portion of the gait phase that the measured EMG level is less than the minimum EMG threshold intensity, and wherein a maximum EMG threshold intensity for the peroneal muscle group 34 in the pre-swing gait phase 262 is 120 mV, causing a third feedback signal (YELLOW) 214 for a portion of the gait phase that the measured EMG level is greater than the maximum EMG threshold intensity.

(41) In a further variant, a maximum EMG threshold intensity for the peroneal muscle group 34 in the early swing gait phase 266 is 60 mV, causing a fourth feedback signal (RED) 218 for a portion of the gait phase that the measured EMG level is greater than the maximum EMG threshold intensity indicating an out-of-phase condition 158.

(42) In still a further variant, a maximum EMG threshold intensity for the peroneal muscle group 34 in the late swing gait phase 270 is 60 mV, causing a fourth feedback signal (RED) 218 for a portion of the gait phase that the measured EMG level is greater than the maximum EMG threshold intensity indicating an out-of-phase condition 158.

(43) In yet a further variant, a minimum EMG threshold intensity for the knee extensors muscle group 38 in the weight acceptance gait phase 250 is 162 millivolts (mV), causing a second feedback signal (GRAY) 210 for a portion of the gait phase that the measured EMG level is less than the minimum EMG threshold intensity, and wherein a maximum EMG threshold intensity for the knee extensors muscle group 38 in the weight acceptance gait phase 250 is 456 mV, causing a third feedback signal (YELLOW) 214 for a portion of the gait phase that the measured EMG level is greater than the maximum EMG threshold intensity.

(44) In another variant of the invention, a minimum EMG threshold intensity for the knee extensors muscle group 38 in the early single support gait phase 254 is 147 mV, causing a second feedback signal (GRAY) 210 for a portion of the gait phase that the measured EMG level is less than the minimum EMG threshold intensity, and wherein a maximum EMG threshold intensity for the knee extensors muscle group 38 in the early single support gait phase 254 is 441 mV, causing a third feedback signal (YELLOW) 214 for a portion of the gait phase that the measured EMG level is greater than the maximum EMG threshold intensity.

(45) In still another variant of the invention, a maximum EMG threshold intensity for the knee extensors muscle group 38 in the late single support gait phase 258 is 353 mV, causing a fourth feedback signal (RED) 218 for a portion of the gait phase that the measured EMG level is greater than the maximum EMG threshold intensity indicating an out-of-phase condition 158.

(46) In yet another variant, a maximum EMG threshold intensity for the knee extensors muscle group 38 in the pre-swing gait phase 262 is 309 mV, causing a fourth feedback signal (RED) 218 for a portion of the gait phase that the measured EMG level is greater than the maximum EMG threshold intensity indicating an out-of-phase condition 158.

(47) In a further variant, a maximum EMG threshold intensity for the knee extensors muscle group 38 in the early swing gait phase 266 is 147 mV, causing a fourth feedback signal (RED) 218 for a portion of the gait phase that the measured EMG level is greater than the maximum EMG threshold intensity indicating an out-of-phase condition 158.

(48) In still a further variant, a minimum EMG threshold intensity for the knee extensors muscle group 38 in the late swing gait phase 270 is 44 mV, causing a second feedback signal (GRAY) 210 for a portion of the gait phase that the measured EMG level is less than the minimum EMG threshold intensity, and wherein a maximum EMG threshold intensity for the knee extensors muscle group 38 in the late swing gait phase 270 is 235 mV, causing a third feedback signal (YELLOW) 214 for a portion of the gait phase that the measured EMG level is greater than the maximum EMG threshold intensity.

(49) In yet a further variant, a minimum EMG threshold intensity for the hamstrings muscle group 42 in the weight acceptance gait phase 250 is 118 millivolts (mV), causing a second feedback signal (GRAY) 210 for a portion of the gait phase that the measured EMG level is less than the minimum EMG threshold intensity, and wherein a maximum EMG threshold intensity for the hamstrings muscle group 42 in the weight acceptance gait phase 250 is 235 mV, causing a third feedback signal (YELLOW) 214 for a portion of the gait phase that the measured EMG level is greater than the maximum EMG threshold intensity.

(50) In another variant of the invention, a minimum EMG threshold intensity for the hamstrings muscle group 42 in the early single support gait phase 254 is 53 mV, causing a second feedback signal (GRAY) 210 for a portion of the gait phase that the measured EMG level is less than the minimum EMG threshold intensity, and wherein a maximum EMG threshold intensity for the hamstrings muscle group 42 in the early single support gait phase 254 is 188 mV, causing a third feedback signal (YELLOW) 214 for a portion of the gait phase that the measured EMG level is greater than the maximum EMG threshold intensity.

(51) In still another variant, a maximum EMG threshold intensity for the hamstrings muscle group 42 in the late single support gait phase 258 is 176 mV, causing a fourth feedback signal (RED) 218 for a portion of the gait phase that the measured EMG level is greater than the maximum EMG threshold intensity indicating an out-of-phase condition 158.

(52) In yet another variant, a maximum EMG threshold intensity for the hamstrings muscle group 42 in the pre-swing gait phase 262 is 103 mV, causing a fourth feedback signal (RED) 218 for a portion of the gait phase that the measured EMG level is greater than the maximum EMG threshold intensity indicating an out-of-phase condition 158.

(53) In a further variant, a minimum EMG threshold intensity for the hamstrings muscle group 42 in the early swing gait phase 266 is 22 mV, causing a second feedback signal (GRAY) 210 for a portion of the gait phase that the measured EMG level is less than the minimum EMG threshold intensity, and wherein a maximum EMG threshold intensity for the hamstrings muscle group 42 in the early swing gait phase 266 is 105 mV, causing a third feedback signal (YELLOW) 214 for a portion of the gait phase that the measured EMG level is greater than the maximum EMG threshold intensity.

(54) In still a further variant, a minimum EMG threshold intensity for the hamstrings muscle group 42 in the late swing gait phase 270 is 44 mV, causing a second feedback signal (GRAY) 210 for a portion of the gait phase that the measured EMG level is less than the minimum EMG threshold intensity, and wherein a maximum EMG threshold intensity for the hamstrings muscle group 42 in the late swing gait phase 270 is 132 mV, causing a third feedback signal (YELLOW) 214 for a portion of the gait phase that the measured EMG level is greater than the maximum EMG threshold intensity.

(55) In yet a further variant, a wherein a maximum EMG threshold intensity for the hip flexors muscle group 46 in the weight acceptance gait phase 250 is 260 mV, causing a fourth feedback signal (RED) 218 for a portion of the gait phase that the measured EMG level is greater than the maximum EMG threshold intensity indicating an out-of-phase condition 158.

(56) In another variant of the invention, a maximum EMG threshold intensity for the hip flexors muscle group 46 in the early single support gait phase 254 is 255 mV, causing a fourth feedback signal (RED) 218 for a portion of the gait phase that the measured EMG level is greater than the maximum EMG threshold intensity indicating an out-of-phase condition 158.

(57) In still another variant, a maximum EMG threshold intensity for the hip flexors muscle group 46 in the late single support gait phase 258 is 250 mV, causing a fourth feedback signal (RED) 218 for a portion of the gait phase that the measured EMG level is greater than the maximum EMG threshold intensity indicating an out-of-phase condition 158.

(58) In yet another variant, a minimum EMG threshold intensity for the hip flexors muscle group 46 in the pre-swing gait phase 262 is 15 mV, causing a second feedback signal (GRAY) 210 for a portion of the gait phase that the measured EMG level is less than the minimum EMG threshold intensity, and wherein a maximum EMG threshold intensity for the hip flexors muscle group 46 in the pre-swing gait phase 262 is 265 mV, causing a third feedback signal (YELLOW) 214 for a portion of the gait phase that the measured EMG level is greater than the maximum EMG threshold intensity.

(59) In a further variant, a minimum EMG threshold intensity for the hip flexors muscle group 46 in the early swing gait phase 266 is 29 mV, causing a second feedback signal (GRAY) 210 for a portion of the gait phase that the measured EMG level is less than the minimum EMG threshold intensity, and wherein a maximum EMG threshold intensity for the hip flexors muscle group 46 in the early swing gait phase 266 is 294 mV, causing a third feedback signal (YELLOW) 214 for a portion of the gait phase that the measured EMG level is greater than the maximum EMG threshold intensity.

(60) In still a further variant, a maximum EMG threshold intensity for the hip flexors muscle group 46 in the late swing gait phase 270 is 235 mV, causing a third feedback signal (YELLOW) 214 for a portion of the gait phase that the measured EMG level is greater than the maximum EMG threshold intensity.

(61) In yet a further variant, a minimum EMG threshold intensity for the hip extensors muscle group 50 in the weight acceptance gait phase 250 is 123 millivolt (mV), causing a second feedback signal (GRAY) 210 for a portion of the gait phase that the measured EMG level is less than the minimum EMG threshold intensity, and wherein a maximum EMG threshold intensity for the hip extensors muscle group 50 in the weight acceptance gait phase 250 is 241 mV, causing a third feedback signal (YELLOW) 214 for a portion of the gait phase that the measured EMG level is greater than the maximum EMG threshold intensity.

(62) In another variant of the invention, a minimum EMG threshold intensity for the hip extensors muscle group 50 in the early single support gait phase 254 is 65 mV, causing a second feedback signal (GRAY) 210 for a portion of the gait phase that the measured EMG level is less than the minimum EMG threshold intensity, and wherein a maximum EMG threshold intensity for the hip extensors muscle group 50 in the early single support gait phase 254 is 194 mV, causing a third feedback signal (YELLOW) 214 for a portion of the gait phase that the measured EMG level is greater than the maximum EMG threshold intensity.

(63) In still another variant, a minimum EMG threshold intensity for the hip extensors muscle group 50 in the late single support gait phase 258 is 10 mV, causing a second feedback signal (GRAY) 210 for a portion of the gait phase that the measured EMG level is less than the minimum EMG threshold intensity, and wherein a maximum EMG threshold intensity for the hip extensors muscle group 50 in the late single support gait phase 258 is 170 mV, causing a third feedback signal (YELLOW) 214 for a portion of the gait phase that the measured EMG level is greater than the maximum EMG threshold intensity.

(64) In yet another variant, a maximum EMG threshold intensity for the hip extensors muscle group 50 in the pre-swing gait phase 262 is 103 mV, causing a fourth feedback signal (RED) 218 for a portion of the gait phase that the measured EMG level is greater than the maximum EMG threshold intensity indicating an out-of-phase condition 158.

(65) In a further variant, a maximum EMG threshold intensity for the hip extensors muscle group 50 in the early swing gait phase 266 is 105 mV, causing a fourth feedback signal (RED) 218 for a portion of the gait phase that the measured EMG level is greater than the maximum EMG threshold intensity indicating an out-of-phase condition 158.

(66) In still a further variant, a maximum EMG threshold intensity for the hip extensors muscle group 50 in the late swing gait phase 270 is 147 mV, causing a fourth feedback signal (RED) 218 for a portion of the gait phase that the measured EMG level is greater than the maximum EMG threshold intensity indicating an out-of-phase condition 158.

(67) In yet a further variant, a maximum EMG threshold intensity for the hip adductors muscle group 54 in the weight acceptance gait phase 250 is 103 millivolts (mV), causing a fourth feedback signal (RED) 218 for a portion of the gait phase that the measured EMG level is greater than the maximum EMG threshold intensity indicating an out-of-phase condition 158.

(68) In another variant of the invention, a maximum EMG threshold intensity for the hip adductors muscle group 54 in the early single support gait phase 254 is 88 mV, causing a fourth feedback signal (RED) 218 for a portion of the gait phase that the measured EMG level is greater than the maximum EMG threshold intensity indicating an out-of-phase condition 158.

(69) In still another variant, a maximum EMG threshold intensity for the hip adductors muscle group 54 in the late single support gait phase 258 is 88 mV, causing a third feedback signal (YELLOW) 214 for a portion of the gait phase that the measured EMG level is greater than the maximum EMG threshold intensity.

(70) In yet another variant, a minimum EMG threshold intensity for the hip adductors muscle group 54 in the pre-swing gait phase 262 is 28 mV, causing a second feedback signal (GRAY) 210 for a portion of the gait phase that the measured EMG level is less than the minimum EMG threshold intensity, and wherein a maximum EMG threshold intensity for the hip adductors muscle group 54 in the pre-swing gait phase 262 is 235 mV, causing a third feedback signal (YELLOW) 214 for a portion of the gait phase that the measured EMG level is greater than the maximum EMG threshold intensity.

(71) In a further variant, a minimum EMG threshold intensity for the hip adductors muscle group 54 in the early swing gait phase 266 is 44 mV, causing a second feedback signal (GRAY) 210 for a portion of the gait phase that the measured EMG level is less than the minimum EMG threshold intensity, and wherein a maximum EMG threshold intensity for the hip adductors muscle group 54 in the early swing gait phase 266 is 265 mV, causing a third feedback signal (YELLOW) 214 for a portion of the gait phase that the measured EMG level is greater than the maximum EMG threshold intensity.

(72) In still a further variant, a maximum EMG threshold intensity for the hip adductors muscle group 54 in the late swing gait phase 270 is 221 mV, causing a third feedback signal (YELLOW) 214 for a portion of the gait phase that the measured EMG level is greater than the maximum EMG threshold intensity.

(73) In yet a further variant, a minimum EMG threshold intensity for the hip abductors muscle group 58 in the weight acceptance gait phase 250 is 59 millivolts (mV), causing a second feedback signal (GRAY) 210 for a portion of the gait phase that the measured EMG level is less than the minimum EMG threshold intensity, and wherein a maximum EMG threshold intensity for the hip abductors muscle group 58 in the weight acceptance gait phase 250 is 412 mV, causing a third feedback signal (YELLOW) 214 for a portion of the gait phase that the measured EMG level is greater than the maximum EMG threshold intensity.

(74) In another variant of the invention, a minimum EMG threshold intensity for the hip abductors muscle group 58 in the early single support gait phase 254 is 132 mV, causing a second feedback signal (GRAY) 210 for a portion of the gait phase that the measured EMG level is less than the minimum EMG threshold intensity, and wherein a maximum EMG threshold intensity for the hip abductors muscle group 58 in the early single support gait phase 254 is 309 mV, causing a third feedback signal (YELLOW) 214 for a portion of the gait phase that the measured EMG level is greater than the maximum EMG threshold intensity.

(75) In still another variant, a maximum EMG threshold intensity for the hip abductors muscle group 58 in the late single support gait phase 258 is 162 mV, causing a fourth feedback signal (RED) 218 for a portion of the gait phase that the measured EMG level is greater than the maximum EMG threshold intensity indicating an out-of-phase condition 158.

(76) In yet another variant, a maximum EMG threshold intensity for the hip abductors muscle group 58 in the pre-swing gait phase 262 is 147 mV, causing a fourth feedback signal (RED) 218 for a portion of the gait phase that the measured EMG level is greater than the maximum EMG threshold intensity indicating an out-of-phase condition 158.

(77) In a further variant, a maximum EMG threshold intensity for the hip abductors muscle group 58 in the early swing gait phase 266 is 132 mV, causing a fourth feedback signal (RED) 218 for a portion of the gait phase that the measured EMG level is greater than the maximum EMG threshold intensity indicating an out-of-phase condition 158.

(78) In a final variant of the invention, a maximum EMG threshold intensity for the hip abductors muscle group 58 in the late swing gait phase 270 is 132 mV, causing a third feedback signal (YELLOW) 214 for a portion of the gait phase that the measured EMG level is greater than the maximum EMG threshold intensity.

The gait training device 10 has been described with reference to particular embodiments. Other modifications and enhancements can be made without departing from the spirit and scope of the claims that follow.

The invention claimed is:
1. A gait training device comprising:
at least one surface electrode, said at least one surface electrode configured to be attached adjacent at least one muscle group of a device user, said at least one surface electrode configured to measure muscle activity as electromyogram levels (EMG);
said at least one muscle group being selected from a group consisting of ankle plantar flexors muscle group, dorsiflexors muscle group, peroneal muscles group, knee extensors muscle group, primary knee flexors muscle group, hip flexors muscle group, primary hip extensors muscle group, hip adductors muscle group and hip abductors muscle group;

first and second footswitch units, said first and second footswitch units configured as shoe insoles and being sized and shaped to fit beneath each foot of said device user, each of said first and second footswitch units having at least one footswitch disposed at at least one location on said first and second footswitch units;

said at least one location being selected from locations adjacent regions of a device user's heel (HEEL), 5th metatarsal head (5MT), 1st metatarsal head (1MT), and great toe (TOE) regions to indicate when said regions of a device user's foot are putting pressure on a walking surface;

first and second telemetry units, said first and second telemetry units configured to be attached to legs of said device user and being electrically connected to said at least one surface electrode and said at least one footswitch unit;

a computer, said computer having a telemetry data receiving device, input devices, data storage and audio and video output devices;

a computer program, said computer program installed on said computer and using data from said first and second footswitch units and said at least one surface electrode received through said telemetry data receiving device to develop feedback information for said device user;

wherein said feedback information comprises real-time data relating to muscle activity (EMG) less than a minimum EMG threshold intensity for a muscle group of said at least one muscle group, more than a maximum EMG threshold intensity for a muscle group of said at least one muscle group, and muscle activity that is out-of-phase correlated with real-time data from said first and second footswitch units; and an apparatus configured to provide said feedback information to said device user.

2. The gait training device of claim 1, wherein said feedback information is also provided to a therapist for said device user.

3. The gait training device of claim 2, wherein said apparatus for providing said feedback information to said device user comprises a video monitor, said video monitor disposed in sight of said device user and receiving said feedback information in a video format, said video format comprising a first feedback signal (BLACK), a second feedback signal (GREY), a third feedback signal (YELLOW) and a fourth feedback signal (RED).

4. The gait training device of claim 2, wherein said apparatus for providing said feedback information to said device user comprises either of headphones or a speaker system, said headphones or speaker system receiving said feedback information in an audio format and providing said feedback information said device user, said audio format comprising a first feedback signal (SILENCE), a second feedback signal (FIRST TONE), a third feedback signal (SECOND TONE) and a fourth feedback signal (THIRD TONE).

5. The gait training device of claim 1, further comprising a treadmill, said treadmill providing the walking surface for said device user.

6. The gait training device of claim 1, further comprising an overhead suspension system, said overhead suspension system configured to off-load a portion of body weight of said device user during therapy.

7. The gait training device of claim 1, wherein a footswitch positioned adjacent said device user's heel is movable with respect to other footswitches in said first and second footswitch units to accommodate device users with different size feet.

8. The gait training device of claim 3, wherein said feedback information for muscle activity for a muscle group, of said at least one muscle group, with a measured EMG level less than a minimum EMG threshold intensity for said muscle group provides a display for said device user that transitions from said first feedback signal (BLACK) to said second feedback signal (GRAY).

9. The gait training device of claim 3, wherein said feedback information for muscle activity for a muscle group, of said at least one muscle group, with a measured EMG level more than a maximum EMG threshold intensity for said muscle group provides a display for said device user that transitions from said first feedback signal (BLACK) to said third feedback signal (YELLOW).

10. The gait training device of claim 3, wherein said feedback information for muscle activity that is out-of-phase provides a display for said device user that transitions from said first feedback signal (BLACK) to said fourth feedback signal (RED) to indicates an out-of-phase condition.

11. The gait training device of claim 4, wherein said feedback information for muscle activity for a muscle group, of said at least one muscle group, with a measured EMG level less than a minimum EMG threshold intensity for said muscle group provides an auditory signal for said device user that transitions from said first feedback signal (SILENCE) to said second feedback signal (FIRST TONE).

12. The gait training device of claim 4, wherein said feedback information for muscle activity for a muscle group, of said at least one muscle group, with a measured EMG level more than a maximum EMG threshold intensity for said muscle group provides an auditory signal for said device user that transitions from said first feedback signal (SILENCE) to said third feedback signal (SECOND TONE).

13. The gait training device of claim 4, wherein said feedback information for muscle activity that is out-of-phase provides an auditory signal for said device user that transitions from said first feedback signal (SILENCE) to said second feedback signal (THIRD TONE) to indicate an out-of-phase condition.

14. The gait training device of claim 3, wherein said computer program provides an input screen for use by a therapist to indicate a leg and which of said at least one muscle group will be used by said computer program to provide feedback information.

15. The gait training device of claim 3, wherein feedback information is provided for each phase of said device user's gait, said phases identified as: weight acceptance, early single support, late single support, pre-swing, early swing and late swing.

16. The gait training device of claim 15, wherein said weight acceptance phase is indicated by footswitch data wherein ipsilateral HEEL AND contralateral TOE footswitches are on OR ipsilateral 5MT AND contralateral TOE footswitches are on OR ipsilateral 1MT and contralateral TOE footswitches are on.

17. The gait training device of claim 15, wherein said early single support phase is indicated by footswitch data wherein ipsilateral HEEL OR ipsilateral 5MT OR ipsilateral 1MT footswitches are on AND NOT contralateral HEEL OR contralateral 5MT OR contralateral 1MT OR contralateral TOE footswitches are on.

18. The gait training device of claim 15, wherein said late single support phase is indicated by footswitch data wherein ipsilateral HEEL OR ipsilateral 5MT OR ipsilateral 1MT OR ipsilateral TOE footswitches are on AND NOT contralateral HEEL OR contralateral 5MT OR contralateral 1MT OR contralateral TOE footswitches are on.

19. The gait training device of claim 15, wherein said pre-swing phase is indicated by footswitch data wherein ipsilateral TOE OR ipsilateral 5MT OR ipsilateral 1MT footswitches are on AND contralateral HEEL OR contralateral 5MT OR contralateral 1MT footswitches are on AND NOT ipsilateral HEEL footswitch is NOT on AND NOT contralateral TOE footswitch is on.

20. The gait training device of claim 15, wherein said early swing phase is indicated by footswitch data wherein contralateral HEEL OR contralateral 5MT OR contralateral 1MT footswitches are on AND NOT ipsilateral HEEL OR ipsilateral 5MT OR ipsilateral 1MT OR ipsilateral TOE footswitches are on.

21. The gait training device of claim 15, wherein said late swing phase is indicated by footswitch data wherein contralateral 5MT OR contralateral 1MT OR contralateral TOE footswitches are on AND NOT ipsilateral HEEL OR ipsilateral 5MT OR ipsilateral 1MT OR ipsilateral TOE footswitches are on.

22. The gait training device of claim 16, wherein an equinas gait condition is indicated by footswitch data during the weight acceptance phase wherein ipsilateral TOE OR ipsilateral 5MT OR ipsilateral 1MT footswitches are on AND contralateral 5MT OR contralateral 1MT OR contralateral TOE footswitches are on AND NOT ipsilateral HEEL footswitch is on, said footswitch data being used to provide negative feedback (ORANGE) to either of said device user and a therapist.

23. The gait training device of claim 2, wherein a contralateral single support phase for reinforcement purposes is indicated by footswitch data wherein contralateral HEEL OR contralateral 5MT OR contralateral 1MT OR contralateral TOE footswitches are on AND NOT ipsilateral HEEL OR ipsilateral 5MT OR ipsilateral 1MT OR ipsilateral TOE footswitches are on and an ispilateral single support phase for reinforcement purposes is indicated by footswitch data wherein ipsilateral HEEL OR ipsilateral 5MT OR ipsilateral 1MT OR ipsilateral TOE footswitches are on AND NOT contralateral HEEL OR contralateral 5MT OR contralateral 1MT OR contralateral TOE footswitches are on.

24. The gait training device of claim 23, wherein a threshold duration of said contralateral single support phase is determined and compared to a duration of said ispilateral single support phase and when said ispilateral single support phase exceeds said threshold duration of said contralateral single support phase a positive feedback signal (GREEN) is generated and provided to at least one of said device user and a therapist.

25. The gait training device of claim 16, wherein a maximum EMG threshold intensity for said plantar flexors muscle group in said weight acceptance phase is 59 microvolts (mV), causing said fourth feedback signal (RED) for a portion of said weight acceptance phase that a measured EMG level is greater than said maximum EMG threshold intensity indicating an out-of-phase condition.

26. The gait training device of claim 17, wherein a minimum EMG threshold intensity for said ankle plantar flexors muscle group in said early single support phase is 74 mV, causing said second feedback signal (GRAY) for a portion of said early single support phase that a measured EMG level is less than said minimum EMG threshold intensity, and wherein a maximum EMG threshold intensity for said ankle plantar flexors muscle group in said early single support phase is 118 mV, causing said third feedback signal (YELLOW) for a portion of said early single support phase that said measured EMG level is greater than said maximum EMG threshold intensity.

27. The gait training device of claim 18, wherein a minimum EMG threshold intensity for said ankle plantar flexors muscle group in said late single support phase is 153 mV, causing said second feedback signal (GRAY) for a portion of said late single support phase that a measured EMG level is less than said minimum EMG threshold intensity, and wherein a maximum EMG threshold intensity for said ankle plantar flexors muscle group in said late single support phase is 191 mV, causing said third feedback signal (YELLOW) for a portion of said late single support phase that said measured EMG level is greater than said maximum EMG threshold intensity.

28. The gait training device of claim 19, wherein a minimum EMG threshold intensity for said ankle plantar flexors muscle group in said pre-swing phase is 88 mV, causing said second feedback signal (GRAY) for a portion of said pre-swing phase that a measured EMG level is less than said minimum EMG threshold intensity, and wherein a maximum EMG threshold intensity for said ankle plantar flexors muscle group in said pre-swing phase is 132 mV, causing said third feedback signal (YELLOW) for a portion of said pre-swing phase that said measured EMG level is greater than said maximum EMG threshold intensity.

29. The gait training device of claim 20, wherein a maximum EMG threshold intensity for said ankle plantar flexors muscle group in said early swing phase is 59 mV, causing said fourth feedback signal (RED) for a portion of said early swing phase that a measured EMG level is greater than said maximum EMG threshold intensity indicating an out-of-phase condition.

30. The gait training device of claim 21, wherein a maximum EMG threshold intensity for said ankle plantar flexors muscle group in said late swing phase is 59 mV, causing said fourth feedback signal (RED) for a portion of said late swing phase that a measured EMG level is greater than said maximum EMG threshold intensity indicating an out-of-phase condition.

31. The gait training device of claim 16, wherein a minimum EMG threshold intensity for said dorsiflexors muscle group in said weight acceptance phase is 120 microvolts (mV), causing a second feedback signal (GRAY) for a portion of said weight acceptance phase that a measured EMG level is less than said minimum EMG threshold intensity.

32. The gait training device of claim 17, wherein a maximum EMG threshold intensity for said dorsiflexors muscle group in said early single support phase is 280 mV, causing a third feedback signal (YELLOW) for a portion of said early single support phase that a measured EMG level is greater than said maximum EMG threshold intensity.

33. The gait training device of claim 18, wherein a maximum EMG threshold intensity for said dorsiflexors muscle group in said late single support phase is 280 mV, causing a third feedback signal (YELLOW) for a portion of said late single support phase that a measured EMG level is greater than said maximum EMG threshold intensity.

34. The gait training device of claim 19, wherein a maximum EMG threshold intensity for said dorsiflexors muscle group in said pre-swing phase is 260 mV, causing a third feedback signal (YELLOW) for a portion of said pre-swing phase that a measured EMG level is greater than said maximum EMG threshold intensity.

35. The gait training device of claim 20, wherein a minimum EMG threshold intensity for said dorsiflexors muscle group in said early swing phase is 118 mV, causing a second feedback signal (GRAY) for a portion of said early swing phase that a measured EMG level is less than said minimum EMG threshold intensity, and wherein a maximum EMG threshold intensity for said dorsiflexors muscle group in said early swing phase is 880 mV, causing a third feedback signal (YELLOW) for a portion of said early swing phase that said measured EMG level is greater than said maximum EMG threshold intensity.

36. The gait training device of claim 21, wherein a minimum EMG threshold intensity for said dorsiflexors muscle group in said late swing phase is 120 mV, causing a second feedback signal (GRAY) for a portion of said late swing phase that a measured EMG level is less than said minimum EMG threshold intensity, and wherein a maximum EMG threshold intensity for said dorsiflexors muscle group in said late swing phase is 882 mV, causing a third feedback signal (YELLOW) for a portion of said late swing phase that said measured EMG level is greater than said maximum EMG threshold intensity.

37. The gait training device of claim 16, wherein a maximum EMG threshold intensity for said peroneal muscles group in said weight acceptance phase is 44 millivolts (mV), causing a fourth feedback signal (RED) for a portion of said weight acceptance phase that a said measured EMG level is greater than said maximum EMG threshold intensity indicating an out-of-phase condition.

38. The gait training device of claim 17, wherein a minimum EMG threshold intensity for said peroneal muscles group in said early single support phase is 74 mV, causing a second feedback signal (GRAY) for a portion of said early single support phase that a measured EMG level is less than said minimum EMG threshold intensity, and wherein a maximum EMG threshold intensity for said peroneal muscles group in said early single support phase is 103 mV, causing a third feedback signal (YELLOW) for a portion of said early single support phase that said measured EMG level is greater than said maximum EMG threshold intensity.

39. The gait training device of claim 18, wherein a minimum EMG threshold intensity for said peroneal muscles group in said late single support phase is 118 mV, causing a second feedback signal (GRAY) for a portion of said late single support phase that a measured EMG level is less than said minimum EMG threshold intensity, and wherein a maximum EMG threshold intensity for said peroneal muscles group in said late single support phase is 176 mV, causing a third feedback signal (YELLOW) for a portion of said late single support phase that said measured EMG level is greater than said maximum EMG threshold intensity.

40. The gait training device of claim 19, wherein a minimum EMG threshold intensity for said peroneal muscles group in said pre-swing phase is 65 mV, causing a second feedback signal (GRAY) for a portion of said pre-swing phase that a measured EMG level is less than said minimum EMG threshold intensity, and wherein a maximum EMG threshold intensity for said peroneal muscles group in said pre-swing phase is 120 mV, causing a third feedback signal (YELLOW) for a portion of said pre-swing phase that said measured EMG level is greater than said maximum EMG threshold intensity.

41. The gait training device of claim 20, wherein a maximum EMG threshold intensity for said peroneal muscles group in said early swing phase is 60 mV, causing a fourth feedback signal (RED) for a portion of said early swing phase that a measured EMG level is greater than said maximum EMG threshold intensity indicating an out-of-phase condition.

42. The gait training device of claim 21, wherein a maximum EMG threshold intensity for said peroneal muscles group in said late swing phase is 60 mV, causing a fourth feedback signal (RED) for a portion of said late swing phase that a measured EMG level is greater than said maximum EMG threshold intensity indicating an out-of-phase condition.

43. The gait training device of claim 16, wherein a minimum EMG threshold intensity for said knee extensors muscle group in said weight acceptance phase is 162 millivolts (mV), causing a second feedback signal (GRAY) for a portion of said weight acceptance phase that a measured EMG level is less than said minimum EMG threshold intensity, and wherein a maximum EMG threshold intensity for said knee extensors muscle group in said weight acceptance phase is 456 mV, causing a third feedback signal (YELLOW) for a portion of said weight acceptance phase that said measured EMG level is greater than said maximum EMG threshold intensity.

44. The gait training device of claim 17, wherein a minimum EMG threshold intensity for said knee extensors muscle group in said early single support gait phase is 147 mV, causing a second feedback signal (GRAY) for a portion of said gait phase that said measured EMG level is less than said minimum EMG threshold intensity, and wherein a maximum EMG threshold intensity for said knee extensors muscle group in said early single support gait phase is 441 mV, causing a third feedback signal (YELLOW) for a portion of said gait phase that said measured EMG level is greater than said maximum EMG threshold intensity.

45. The gait training device of claim 18, wherein a maximum EMG threshold intensity for said knee extensors muscle group in said late single support phase is 353 mV, causing a fourth feedback signal (RED) for a portion of said late single support phase that a measured EMG level is greater than said maximum EMG threshold intensity indicating an out-of-phase condition.

46. The gait training device of claim 19, wherein a maximum EMG threshold intensity for said knee extensors muscle group in said pre-swing phase is 309 mV, causing a fourth feedback signal (RED) for a portion of said pre-swing phase that a measured EMG level is greater than said maximum EMG threshold intensity indicating an out-of-phase condition.

47. The gait training device of claim 20, wherein a maximum EMG threshold intensity for said knee extensors muscle group in said early swing phase is 147 mV, causing a fourth feedback signal (RED) for a portion of said early swing phase that a measured EMG level is greater than said maximum EMG threshold intensity indicating an out-of-phase condition.

48. The gait training device of claim 21, wherein a minimum EMG threshold intensity for said knee extensors muscle group in said late swing phase is 44 mV, causing a second feedback signal (GRAY) for a portion of said late swing phase that a measured EMG level is less than said minimum EMG threshold intensity, and wherein a maximum EMG threshold intensity for said knee extensors muscle group in said late swing phase is 235 mV, causing a third feedback signal (YELLOW) for a portion of said late swing phase that said measured EMG level is greater than said maximum EMG threshold intensity.

49. The gait training device of claim 16, wherein a minimum EMG threshold intensity for said primary knee flexors muscle group in said weight acceptance phase is 118 millivolts (mV), causing a second feedback signal (GRAY) for a portion of said weight acceptance phase that a measured EMG level is less than said minimum EMG threshold intensity, and wherein a maximum EMG threshold intensity for said primary knee flexors muscle group in said weight acceptance phase is 235 mV, causing a third feedback signal (YELLOW) for a portion of said weight acceptance phase that said measured EMG level is greater than said maximum EMG threshold intensity.

50. The gait training device of claim 17, wherein a minimum EMG threshold intensity for said primary knee flexors muscle group in said early single support phase is 53 mV, causing a second feedback signal (GRAY) for a portion of said early single support phase that a measured EMG level is less than said minimum EMG threshold intensity, and wherein a maximum EMG threshold intensity for said primary knee flexors muscle group in said early single support phase is 188 mV, causing a third feedback signal (YELLOW) for a portion of said early single support phase that said measured EMG level is greater than said maximum EMG threshold intensity.

51. The gait training device of claim 18, wherein a maximum EMG threshold intensity for said primary knee flexors muscle group in said late single support phase is 176 mV, causing a fourth feedback signal (RED) for a portion of said late single support phase that a said measured EMG level is greater than said maximum EMG threshold intensity indicating an out-of-phase condition.

52. The gait training device of claim 19, wherein a maximum EMG threshold intensity for said primary knee flexors muscle group in said pre-swing phase is 103 mV, causing a fourth feedback signal (RED) for a portion of said pre-swing phase that a said measured EMG level is greater than said maximum EMG threshold intensity indicating an out-of-phase condition.

53. The gait training device of claim 20, wherein a minimum EMG threshold intensity for said primary knee flexors muscle group in said early swing phase is 22 mV, causing a second feedback signal (GRAY) for a portion of said early swing phase that a measured EMG level is less than said minimum EMG threshold intensity, and wherein a maximum EMG threshold intensity for said primary knee flexors muscle group in said early swing phase is 105 mV, causing a third feedback signal (YELLOW) for a portion of said early swing phase that said measured EMG level is greater than said maximum EMG threshold intensity.

54. The gait training device of claim 21, wherein a minimum EMG threshold intensity for said primary knee flexors muscle group in said late swing phase is 44 mV, causing a second feedback signal (GRAY) for a portion of said late swing phase that a measured EMG level is less than said minimum EMG threshold intensity, and wherein a maximum EMG threshold intensity for said primary knee flexors muscle group in said late swing phase is 132 mV, causing a third feedback signal (YELLOW) for a portion of said late swing phase that said measured EMG level is greater than said maximum EMG threshold intensity.

55. The gait training device of claim 16, wherein a wherein a maximum EMG threshold intensity for said hip flexors muscle group in said weight acceptance phase is 260 mV, causing a fourth feedback signal (RED) for a portion of said weight acceptance phase that a measured EMG level is greater than said maximum EMG threshold intensity indicating an out-of-phase condition.

56. The gait training device of claim 17, wherein a maximum EMG threshold intensity for said hip flexors muscle group in said early single support phase is 255 mV, causing a fourth feedback signal (RED) for a portion of said early single support phase that a measured EMG level is greater than said maximum EMG threshold intensity indicating an out-of-phase condition.

57. The gait training device of claim 18, wherein a maximum EMG threshold intensity for said hip flexors muscle group in said late single support phase is 250 mV, causing a fourth feedback signal (RED) for a portion of said late single support phase that a measured EMG level is greater than said maximum EMG threshold intensity indicating an out-of-phase condition.

58. The gait training device of claim 19, wherein a minimum EMG threshold intensity for said hip flexors muscle group in said pre-swing phase is 15 mV, causing a second feedback signal (GRAY) for a portion of said pre-swing phase that a measured EMG level is less than said minimum EMG threshold intensity, and wherein a maximum EMG threshold intensity for said hip flexors muscle group in said pre-swing phase is 265 mV, causing a third feedback signal (YELLOW) for a portion of said pre-swing phase that said measured EMG level is greater than said maximum EMG threshold intensity.

59. The gait training device of claim 20, wherein a minimum EMG threshold intensity for said hip flexors muscle group in said early swing phase is 29 mV, causing a second feedback signal (GRAY) for a portion of said early swing phase that a measured EMG level is less than said minimum EMG threshold intensity, and wherein a maximum EMG threshold intensity for said hip flexors muscle group in said early swing phase is 294 mV, causing a third feedback signal (YELLOW) for a portion of said early swing phase that said measured EMG level is greater than said maximum EMG threshold intensity.

60. The gait training device of claim 21, wherein a maximum EMG threshold intensity for said hip flexors muscle group in said late swing phase is 235 mV, causing a third feedback signal (YELLOW) for a portion of said late swing phase that a measured EMG level is greater than said maximum EMG threshold intensity.

61. The gait training device of claim 16, wherein a minimum EMG threshold intensity for said primary hip extensors muscle group in said weight acceptance phase is 123 millivolt (mV), causing a second feedback signal (GRAY) for a portion of said weight acceptance phase that a said measured EMG level is less than said minimum EMG threshold intensity, and wherein a maximum EMG threshold intensity for said primary hip extensors muscle group in said weight acceptance phase is 241 mV, causing a third feedback signal (YELLOW) for a portion of said weight acceptance phase that said measured EMG level is greater than said maximum EMG threshold intensity.

62. The gait training device of claim 17, wherein a minimum EMG threshold intensity for said primary hip extensors muscle group in said early single support phase is 65 mV, causing a second feedback signal (GRAY) for a portion of said early single support phase that a measured EMG level is less than said minimum EMG threshold intensity, and wherein a maximum EMG threshold intensity for said primary hip extensors muscle group in said early single support phase is 194 mV, causing a third feedback signal (YELLOW) for a portion of said early single support phase that said measured EMG level is greater than said maximum EMG threshold intensity.

63. The gait training device of claim 18, wherein a minimum EMG threshold intensity for said hip extensors muscle group in said late single support phase is 10 mV, causing a second feedback signal (GRAY) for a portion of said late single support phase that a measured EMG level is less than said minimum EMG threshold intensity, and wherein a maximum EMG threshold intensity for said hip extensors muscle group in said late single support phase is 170 mV, causing a third feedback signal (YELLOW) for a portion of said late single support phase that said measured EMG level is greater than said maximum EMG threshold intensity.

64. The gait training device of claim 19, wherein a maximum EMG threshold intensity for said hip extensors muscle group in said pre-swing phase is 103 mV, causing a fourth feedback signal (RED) for a portion of said pre-swing phase that said measured EMG level is greater than said maximum EMG threshold intensity indicating an out-of-phase condition.

65. The gait training device of claim 20, wherein a maximum EMG threshold intensity for said hip extensors muscle group in said early swing phase is 105 mV, causing a fourth feedback signal (RED) for a portion of said early swing phase that a measured EMG level is greater than said maximum EMG threshold intensity indicating an out-of-phase condition.

66. The gait training device of claim 21, wherein a maximum EMG threshold intensity for said hip extensors muscle group in said late swing phase is 147 mV, causing a fourth feedback signal (RED) for a portion of said late swing phase that a measured EMG level is greater than said maximum EMG threshold intensity indicating an out-of-phase condition.

67. The gait training device of claim 16, wherein a maximum EMG threshold intensity for said hip adductors muscle group in said weight acceptance phase is 103 millivolts (mV), causing a fourth feedback signal (RED) for a portion of said weight acceptance phase that a measured EMG level is greater than said maximum EMG threshold intensity indicating an out-of-phase condition.

68. The gait training device of claim 17, wherein a maximum EMG threshold intensity for said hip adductors muscle group in said early single support phase is 88 mV, causing a fourth feedback signal (RED) for a portion of said early single support phase that a measured EMG level is greater than said maximum EMG threshold intensity indicating an out-of-phase condition.

69. The gait training device of claim 18, wherein a maximum EMG threshold intensity for said hip adductors muscle group in said late single support phase is 88 mV, causing a third feedback signal (YELLOW) for a portion of said late single support phase that said measured EMG level is greater than said maximum EMG threshold intensity.

70. The gait training device of claim 19, wherein a minimum EMG threshold intensity for said hip adductors muscle group in said pre-swing phase is 28 mV, causing a second feedback signal (GRAY) for a portion of said pre-swing phase that a measured EMG level is less than said minimum EMG threshold intensity, and wherein a maximum EMG threshold intensity for said hip adductors muscle group in said pre-swing phase is 235 mV, causing a third feedback signal (YELLOW) for a portion of said pre-swing phase that said measured EMG level is greater than said maximum EMG threshold intensity.

71. The gait training device of claim 20, wherein a minimum EMG threshold intensity for said hip adductors muscle group in said early swing phase is 44 mV, causing a second feedback signal (GRAY) for a portion of said early swing phase that a measured EMG level is less than said minimum EMG threshold intensity, and wherein a maximum EMG threshold intensity for said hip adductors muscle group in said early swing phase is 265 mV, causing a third feedback signal (YELLOW) for a portion of said early swing phase that said measured EMG level is greater than said maximum EMG threshold intensity.

72. The gait training device of claim 21, wherein a maximum EMG threshold intensity for said hip adductors muscle group in said late swing phase is 221 mV, causing a third feedback signal (YELLOW) for a portion of said late swing phase that said measured EMG level is greater than said maximum EMG threshold intensity.

73. The gait training device of claim 16, wherein a minimum EMG threshold intensity for said hip abductors muscle group in said weight acceptance phase is 59 millivolts (mV), causing a second feedback signal (GRAY) for a portion of said weight acceptance phase that a measured EMG level is less than said minimum EMG threshold intensity, and wherein a maximum EMG threshold intensity for said hip abductors muscle group in said weight acceptance phase is 412 mV, causing a third feedback signal (YELLOW) for a portion of said weight acceptance phase that said measured EMG level is greater than said maximum EMG threshold intensity.

74. The gait training device of claim 17, wherein a minimum EMG threshold intensity for said hip abductors muscle group in said early single support phase is 132 mV, causing a second feedback signal (GRAY) for a portion of said early single support phase that a measured EMG level is less than said minimum EMG threshold intensity, and wherein a maximum EMG threshold intensity for said hip abductors muscle group in said early single support phase is 309 mV, causing a third feedback signal (YELLOW) for a portion of said early single support phase that said measured EMG level is greater than said maximum EMG threshold intensity.

75. The gait training device of claim 18, wherein a maximum EMG threshold intensity for said hip abductors muscle group in said late single support phase is 162 mV, causing a fourth feedback signal (RED) for a portion of said late single support phase that a measured EMG level is greater than said maximum EMG threshold intensity indicating an out-of-phase condition.

76. The gait training device of claim 19, wherein a maximum EMG threshold intensity for said hip abductors muscle group in said pre-swing phase is 147 mV, causing a fourth feedback signal (RED) for a portion of said pre-swing phase that a measured EMG level is greater than said maximum EMG threshold intensity indicating an out-of-phase condition.

77. The gait training device of claim 20, wherein a maximum EMG threshold intensity for said hip abductors muscle group in said early swing phase is 132 mV, causing a fourth feedback signal (RED) for a portion of said early swing phase that a measured EMG level is greater than said maximum EMG threshold intensity indicating an out-of-phase condition.

78. The gait training device of claim 21, wherein a maximum EMG threshold intensity for said hip abductors muscle group in said late swing phase is 132 mV, causing a third feedback signal (YELLOW) for a portion of said late swing phase that a measured EMG level is greater than said maximum EMG threshold intensity.

* * * * *